US008897549B2

(12) United States Patent
Sakashita et al.

(10) Patent No.: US 8,897,549 B2
(45) Date of Patent: Nov. 25, 2014

(54) MICROSTRUCTURE ANALYSIS METHOD, PROGRAM THEREOF, AND MICROSTRUCTURE ANALYSIS DEVICE

(71) Applicant: NGK Insulators, Ltd., Nagoya (JP)

(72) Inventors: Satoshi Sakashita, Yokkaichi (JP); Shingo Sokawa, Anjyo (JP); Hiroyuki Nagaoka, Kakamigahara (JP); Yuichiro Watanabe, Obu (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 13/974,527

(22) Filed: Aug. 23, 2013

(65) Prior Publication Data
US 2013/0336578 A1 Dec. 19, 2013

Related U.S. Application Data

(63) Continuation of application No. PCT/JP2013/057973, filed on Mar. 21, 2013.

(30) Foreign Application Priority Data

Mar. 30, 2012 (JP) ................. 2012-082540

(51) Int. Cl.
*G06K 9/00* (2006.01)
*G06T 7/00* (2006.01)
*G01N 23/04* (2006.01)
*C04B 38/00* (2006.01)
*C04B 38/06* (2006.01)
*G01N 15/08* (2006.01)

(52) U.S. Cl.
CPC ...... *G06T 7/0051* (2013.01); *G01N 2015/0846* (2013.01); *G01N 2223/649* (2013.01); *G01N 23/046* (2013.01); *G01N 15/088* (2013.01); *C04B 38/00* (2013.01); *C04B 38/06* (2013.01)

USPC .......................................... 382/154; 382/128

(58) Field of Classification Search
USPC ................. 382/128–134, 154, 15; 348/42–60
See application file for complete search history.

(56) References Cited

U.S. PATENT DOCUMENTS 5,275,889 A * 1/1994 Yokouchi et al. ............. 428/426
5,436,980 A * 7/1995 Weeks et al. .................. 382/141

(Continued)

FOREIGN PATENT DOCUMENTS

JP 2001-201465 A1 7/2001
JP 2004-261644 A1 9/2004

(Continued)

OTHER PUBLICATIONS

International Search Report and Written Opinion dated Jun. 11, 2013.

(Continued)

*Primary Examiner* — Alex Liew
(74) *Attorney, Agent, or Firm* — Burr & Brown, PLLC

(57) ABSTRACT

Porous body data in which position information and type information are correlated is reference to take a curved surface solid including a parent virtual sphere and child virtual spheres as a virtual curved surface solid, and place multiple virtual curved surface solids so as to fill in space pixels with curved surface solid pixels occupied by virtual curved surface solids. Repeating this process, by placing multiple virtual curved surface solids within space in a porous body, the microstructure of the porous body is analyzed precisely. As for analysis, deriving of in-plane uniformity index $\gamma_x$, spatial uniformity index $\gamma$, pressure drop P, flow-through velocity T, and equivalent diameter d, for example, and acceptability determination based on derived values thereof, is performed.

22 Claims, 19 Drawing Sheets

(56) References Cited

U.S. PATENT DOCUMENTS

| | | | |
|---|---|---|---|
| 5,588,032 A * | 12/1996 | Johnson et al. | 378/8 |
| 5,717,778 A * | 2/1998 | Chu et al. | 382/133 |
| 6,442,287 B1 * | 8/2002 | Jiang et al. | 382/128 |
| 8,449,603 B2 * | 5/2013 | Weber et al. | 623/1.48 |
| 2005/0018887 A1 * | 1/2005 | Breen | 382/128 |
| 2005/0153356 A1 * | 7/2005 | Okawa et al. | 435/6 |
| 2006/0154817 A1 | 7/2006 | Nomura et al. | |
| 2007/0064985 A1 * | 3/2007 | Chhibber et al. | 382/128 |
| 2007/0064989 A1 * | 3/2007 | Chhibber et al. | 382/128 |
| 2008/0205596 A1 | 8/2008 | Kato | |
| 2009/0141956 A1 * | 6/2009 | Chhibber et al. | 382/128 |
| 2009/0201365 A1 * | 8/2009 | Fukuoka et al. | 348/77 |
| 2011/0004447 A1 * | 1/2011 | Hurley et al. | 703/1 |
| 2012/0163688 A1 * | 6/2012 | Salazar-Tio | 382/131 |
| 2012/0275658 A1 * | 11/2012 | Hurley et al. | 382/109 |
| 2013/0132046 A1 * | 5/2013 | Miyamoto et al. | 703/2 |
| 2013/0336578 A1 * | 12/2013 | Sakashita et al. | 382/154 |

FOREIGN PATENT DOCUMENTS

| | | |
|---|---|---|
| JP | 2005-114612 A | 4/2005 |
| JP | 2005-283547 A1 | 10/2005 |
| JP | 2005-326173 A1 | 11/2005 |
| JP | 2010-138770 A1 | 6/2010 |
| JP | 2011-079732 A1 | 4/2011 |
| JP | 2012-214365 A1 | 11/2012 |

OTHER PUBLICATIONS

European Search Report, European Application No. 13750617, dated May 15, 2014 (6 pages).

Dong, Hu et al., "Pore-network extraction from micro-computerized-tomography images," *Physical Review E*, vol. 80, No. 3, ISSN: 1539-3755, dated Sep. 14, 2009 (11 pages).

Al-Kharusi, Anwas R. et al., "Network extraction from sandstone and carbonate pore space images," *Journal of Petroleum Science and Engineering*, vol. 56, No. 4, ISSN: 0920-4105, dated Apr. 26, 2007 (13 pages).

Silin, Dmitriy et al., "Pore space morphology analysis using maximal inscribed spheres," *Physica A*, vol. 371 No. 2, ISSN: 0378-4371, dated Nov. 15, 2006 (25 pages).

* cited by examiner (a)

(b)

(a)

(b)

Path length $L_f = L0 + L1 + L2 + L3$ (a)

(b)

Path length $L_f = (a+b)/2 + c + \dfrac{d+\{e+(f+g)/2+h\}}{2}$

MICROSTRUCTURE ANALYSIS METHOD, PROGRAM THEREOF, AND MICROSTRUCTURE ANALYSIS DEVICE

BACKGROUND OF THE INVENTION

1. Field of the Invention

The present invention relates to a microstructure analysis method, a program thereof, and a microstructure analysis device.

2. Description of Related Art

As one method to analyze microstructures such as pores in porous bodies, there has been proposed a method where 3 dimensional pixel data of a porous body is obtained by performing a CT scan, and analysis is performed based on this pixel data. For example, PTL 1 describes a pore continuity analysis method in which virtual spheres of various diameters are situated so as to fill in pixels of the pixel data representing space, so as to find continuity of pores from one exposed face of a porous body to another exposed face thereof, based on information relating to the situated virtual spheres.

CITATION LIST

Patent Literature

Patent Literature 1: Japanese Unexamined Patent Application Publication No. 2011-079732

SUMMARY OF THE INVENTION

Technical Problem

However, the method described in PTL 1 only uses virtual spheres to simulate the complicatedly-shaped pores of a porous body. Accordingly, there have been cases where microstructure analysis using virtual spheres situated according to the method in PTL 1 has been found to be insufficient in precision, with regard to performing evaluation of pressure drop and collection performance in a case of use of a porous member as a filter, for example. Accordingly, a microstructure analysis method with higher precision has been desired.

The present invention has been made to solve such problems, and it is a primary object thereof to analyze microstructures of porous bodies more precisely.

Solution to Problem

To achieve the above-described objects, the microstructure analysis method, the program thereof, and the microstructure analysis device, according to the present invention, employ the following means.

The microstructure analysis method according to the present invention is a microstructure analysis method of a porous body, using porous body data in which correlated position information representing position of a pixel obtained by a 3 dimensional scan of the porous body, and pixel type information representing whether a space pixel representing that the pixel is space or a matter pixel representing that the pixel is matter, comprising:

(a) a step to take a curved surface solid including a parent virtual sphere and one or more child virtual spheres with which a portion of pixels occupied by the parent virtual sphere overlap as a virtual curved surface solid, and place the multiple virtual curved surface solids so as to fill in the space pixels with curved surface solid pixels which are pixels occupied by the virtual curved surface solid, referencing the porous body data; and (b) a step to analyze microstructure of the porous body based on information relating to the virtual curved surface solids placed in the step (a).

With this microstructure analysis method, multiple virtual curved surface solids made up of a parent virtual sphere and child virtual spheres are placed so as to fill in space pixels with curved surface solid pixels occupied by the virtual curved surface solids, referencing porous body data in which position information and pixel type information are correlated. Thus, complicated shape space (pores) within the porous body are replaced with virtual curved surface solids of shapes where multiple spheres are combined, so space within the porous body can be better simulated as a group of multiple virtual curved surface solids. The microstructure of the porous body can then be analyzed more precisely by being based on information relating to these virtual curved surface solids. Now, "information relating to virtual curved surface solids" may be information such as center coordinates and diameter and so forth of the parent virtual sphere and child virtual spheres for each virtual curved surface solid, or may be position information of curved surface solid pixels which the virtual curved surface solid occupies. To "analyze a microstructure" may be, for example, to derive a numerical value representing a microstructure of a porous body such as porosity, average pore diameter, and so forth, or may be to derive a value relating to pressure drop property, collection performance, and so forth, of the porous body, or may be to perform evaluation of acceptability for such as pressure drop property, collection performance, and so forth. Also, the number of parent virtual spheres in one virtual curved surface solid may be one, or may be multiple. In the event that there are multiple parent virtual spheres, the virtual curved surface solid may be made up of multiple parent virtual spheres and one or more child virtual spheres of which pixels occupied thereby partially overlap with at least one of the multiple parent virtual spheres. Note that in step (a), in the event that multiple child virtual spheres are to be placed at the time of placing one virtual curved surface solid, the child virtual spheres may be placed so as to not overlap each other, or mutual overlapping thereof may be permitted.

With the microstructure analysis method according to the present invention, in the step (a), the virtual curved surface solid may be placed such that the center of a child virtual sphere configuring the virtual curved surface solid overlaps with the parent virtual sphere configuring the virtual curved surface solid. Also, in the step (a), the multiple virtual curved surface solids may be placed, permitting the virtual curved surface solids to overlap with each other. Thus, virtual curved surface solids with as great a volume as possible can be placed as compared with a case where virtual curved surface solids are placed so as to not overlap with other virtual spheres. Also, in the step (a), the multiple virtual curved surface solids may be placed so that the virtual curved surface solids do not overlap with each other. Further, in the step (a), the virtual curved surface solids may be placed so that the curved surface solid pixels do not overlap with the matter pixels. Placing the virtual curved surface solids so that the virtual curved surface solids do not overlap with each other or so that the curved surface solid pixels do not overlap with the matter pixels restricts the positions where the virtual curved surface solids can be placed, so processing time required to place the virtual curved surface solids can be reduced as compared with a case where overlapping is permitted.

With the microstructure analysis method according to the present invention, in the step (a), processing to place one virtual curved surface solid may be performed by placing the parent virtual sphere having the greatest spherical diameter that can be placed so as to fill in the space pixels, and placing one or more of the child virtual spheres such that pixels occupied by the child virtual spheres partially overlap with pixels occupied by the placed parent virtual sphere and fill in the space pixels, and the multiple virtual curved surface solids are placed by repeating this processing so that virtual curved surface solids are placed in mutually different positions. Thus, space pixels can be filled in with virtual curved surface solids as large as possible.

With the microstructure analysis method according to the present invention, in the step (a), processing to place one virtual curved surface solid may be performed by placing the parent virtual sphere having the greatest spherical diameter that can be placed so as to fill in the space pixels without overlapping with the matter pixels, and placing one or more of the child virtual spheres such that the center of the child virtual spheres overlaps with the placed parent virtual sphere, and such that pixels occupied by the child virtual spheres do not overlap with the matter pixels and fill in the space pixels, and the multiple virtual curved surface solids are placed by repeating this processing so that virtual curved surface solids are placed in mutually different positions, permitting pixels occupied by different virtual curved surface solids to mutually overlap. Thus, virtual curved surface solids as large a volume as possible can be placed, as compared with a case where virtual curved surface solids are placed so as to not overlap with other virtual curved surface solids. Also, the virtual curved surface solids are placed so that the curved surface solid pixels do not overlap with the matter pixels, so processing time required to place the virtual curved surface solids can be reduced as compared with a case where overlapping is permitted. Also, a parent virtual sphere having as large a sphere diameter as possible to be placed can be placed when placing virtual curved surface solids, so the space pixels can be filled in with virtual curved surface solids that have as large a volume as possible.

With the microstructure analysis method according to the present invention, in the step (a), processing to place one virtual curved surface solid may be performed by placing the parent virtual sphere having the greatest spherical diameter that can be placed so as to fill in the space pixels without overlapping with the matter pixels, and placing one or more of the child virtual spheres such that the center of the child virtual spheres overlaps with the placed parent virtual sphere, and such that pixels occupied by the child virtual spheres do not overlap with the matter pixels and fill in the space pixels, and the multiple virtual curved surface solids are placed by repeating this processing so that pixels occupied by different virtual curved surface solids do not mutually overlap. Thus, the virtual curved surface solids are placed so that the virtual curved surface solids themselves or the curved surface solid pixels and the matter pixels do not overlap, so processing time required to place the virtual curved surface solids can be reduced as compared with a case where overlapping is permitted. Also, the space pixels can be filled in with virtual curved surface solids that have as large a volume as possible.

With the microstructure analysis method according to the present invention, in the step (b), based on information relating to the virtual curved surface solids placed in the step (a) the microstructure of the porous body may be analyzed by deriving multiple path lengths $L_f$ from one of a predetermined inflow face and a predetermined outflow face of the porous body to the other face following adjacent or overlapping virtual curved surface solids, deriving an average value $L_{fmean}$ of the multiple path lengths $L_f$, and deriving a pressure drop index $P_e$ by $P_e$=(wetted area $A_W$ of space within porous body/ pore volume $V_p$ of space within porous body)×(1/porosity $\epsilon$ of porous body)×(average value $L_{fmean}$/distance L between inflow face and outflow face). The present inventors have found that a pressure drop index $P_e$ derived in this way has a high correlation with the actual pressure drop of the porous body. Accordingly, the pressure drop property of the porous body, for example, can be predicted or evaluated more precisely, by deriving this pressure drop index $P_e$ by microstructure analysis. Now, the wetted area $A_W$, pore volume $V_p$, and porosity c may be derived based on information relating to the space pixels and matter pixels, or may be calculated based on information relating to the virtual curved surface solids.

In this case, in the step (b), the microstructure of the porous body may be analyzed by deriving pressure drop $P_S$ per unit thickness of the porous body by $P_S$=constant $\alpha \times P_e^2$+constant $\beta \times P_e$. The present inventors have found that the pressure drop $P_S$ per unit thickness of the porous body derived from the pressure drop index $P_e$ in this way approximately matches the actual pressure drop of the porous body. Accordingly, the pressure drop property of the porous body can be predicted or evaluated more precisely, by deriving this pressure drop $P_S$ by microstructure analysis. Note that the constant β is an integer and the constant 13 is a real number. Also, pressure drop $P_S$>0 holds within the range of pressure drop index $P_e$>0.

With the microstructure analysis method according the present invention, in the step (a), processing of placing the multiple virtual curved surface solids, and processing for deriving information relating to flow of a fluid for each space pixel at the time of the fluid passing through the interior of the porous body by performing fluid analysis based on the porous body data, may be performed; and in the step (b), the microstructure of the porous body may be analyzed based on information relating to the placed virtual curved surface solids and the derived information relating to flow. Here, "information relating to flow . . . for each space pixel" may include at least flow velocity (vector or scalar) for each space pixel, or may include at least through-flow volume for each space pixel. "Fluid analysis" may be analysis by the lattice Boltzmann method. Also, for fluid analysis, fluid analysis may be performed regarding a case where there is inflow of fluid from a predetermined inflow face of the porous body, or fluid analysis may be performed regarding a case where there is inflow of fluid from a predetermined inflow face of the porous body to a predetermined outflow face.

With the microstructure analysis method according to an embodiment of the present invention performing the above-described fluid analysis, in the step (a), fluid analysis may be performed regarding a case of inflow of a fluid from a predetermined inflow face of the porous body, and deriving at least flow velocity for each space pixel as the information relating to flow; and in the step (b), the microstructure of the porous body may be analyzed by deriving one or more in-plane uniformity index $\gamma_x$ of flow velocity at a cross-section on the porous body parallel to the inflow face, by the following Expression (1). Now, the more uniform the flow velocity of a fluid at a cross-section is, the greater (closer to value 1) the value of the in-plane uniformity index $\gamma_x$ is, and the greater the irregularity in the flow velocity of a fluid at a cross-section is, the smaller the value is. Also, the present inventors have found that, in a case of using the porous body for a filter, the greater the value of the in-plane uniformity index $\gamma_x$ is, the better the pressure drop property tends to be. Accordingly, deriving this in-plane uniformity index $\gamma_x$ as analysis of a microstructure enables the pressure drop property of the porous body to be predicted and evaluated more precisely. Note that with the step (b), when the derived in-plane uniformity index $\gamma_x$ is at or greater than a predetermined threshold, the pressure drop property of the porous body may be determined to be acceptable. The predetermined threshold may be the value 0.6, for example. Now, the flow velocity at each space pixel may be directly derived by fluid analysis for example, or may be derived by deriving the through-flow volume per unit time at each space pixel by fluid analysis, and the flow velocity being derived from the through-flow volume per unit time that has been derived and the area (cross-sectional area) of the portion of space pixels where the fluid passes through, or the like. Also, with fluid analysis, the flow velocity vector may be derived for each space pixel, with components of the flow velocity vectors which are in a direction perpendicular to the cross-section being taken as the flow velocity for each space pixel.

[Math. 1]

$$\gamma_x = 1 - \frac{1}{2}\sum_{i=1}^{n} \frac{|u_i - u_{mean}| \cdot A_i}{u_{mean} \cdot A} \qquad \text{Expression (1)}$$

where n: number [count] of virtual curved surface solids within cross-section x: distance [m] between cross-section and inflow face $u_i$: average flow velocity (i=1, 2, ..., n) [m/s] for each of the n virtual curved surface solids at cross-section $u_{mean}$: average value (=($u_1+u_2+...+u_n$)/n) [m/s] of average flow velocity $u_i$ at cross-section $A_i$: cross-sectional area (i=1, 2, ..., n) [m²] for each virtual curved surface solid within cross-section A: total cross-sectional area (=$A_1+A_2+...+A_n$) [m²] of virtual curved surface solids at cross-section In this case, in the step (b), the microstructure of the porous body may be analyzed by deriving the in-plane uniformity index $\gamma_x$ regarding the multiple cross-sections of the porous body, and deriving a spatial uniformity index $\gamma$ of flow velocity at the porous body by the following Expression (2) using the derived in-plane uniformity index $\gamma_x$. The spatial uniformity index $\gamma$ thus derived is such that the smaller the irregularity in the in-plane uniformity index $\gamma_x$ derived regarding multiple cross-sections is, the greater the value is, and the greater the irregularities, the smaller the value is. The present inventors have also found that collecting performance in the case of using the porous body for a filter tends to be better the greater the value of this spatial uniformity index $\gamma$ is. Accordingly, by deriving this spatial uniformity index $\gamma$ as analysis of a microstructure enables the collecting performance of the porous body to be predicted and evaluated more precisely, for example. Note that with the step (b), in the event that the derived spatial uniformity index $\gamma$ is at or greater than a predetermined threshold, the collecting performance of the porous body may be determined to be acceptable. The predetermined threshold may be the value 0.5 for example, or may be the value 0.6.

[Math. 2]

$$\gamma = \overline{\gamma_x} \cdot (1 - \delta_\gamma) \qquad \text{Expression (2)}$$

where $\overline{\gamma_x}$: average value of $\gamma_x$ $\delta_\gamma$: standard deviation of $\gamma_x$ With the microstructure analysis method according to an embodiment of the present invention deriving the in-plane uniformity index $\gamma_x$ described above, in the step (b), the microstructure of the porous body may be analyzed by deriving pressure drop P per unit thickness of the porous body by the following Expression (3) using the derived in-plane uniformity index $\gamma_x$. This Expression (3) is one where a known Ergun's Equation representing pressure drop properties at the time of a fluid passing through a porous body, has been revised using the in-plane uniformity index $\gamma_x$. The present inventors have found that the pressure drop P per unit thickness derived in this way has higher correlation with the actual pressure drop of the porous body as compared to pressure drop derived by Ergun's Equation. Accordingly, the pressure drop property of the porous body, for example, can be predicted or evaluated more precisely, by deriving this pressure drop P per unit volume as microstructure analysis. Note that in the event that pressure drop P has been derived corresponding to each of in-plane uniformity indices $\gamma_x$, an average value of multiple pressure drops P may be derived. Also, the pressure drop property of the porous body may be predicted or evaluated from this average value of pressure drops P.

[Math. 3]

$$P = \frac{\Delta P_x}{\Delta x} = \left(\frac{200}{3} \frac{1}{D_{hx}^2 \cdot \varepsilon_k} \mu U_x + \frac{7}{6} \frac{1}{D_{hx} \cdot \varepsilon_x^2} \rho U_x^2\right) \cdot \gamma_x^k \qquad \text{Expression (3)}$$

where $\Delta x$: cross-sectional thickness [m] at cross-section at distance x $\Delta P_x$: pressure drop [Pa] at cross-section at distance x $Dh_x$: representative hydraulic diameter [m] of space (pores) at cross-section at distance x $\varepsilon_x$: voidage (=number of space pixels/(number of space pixels+number of matter pixels)) at cross-section at distance x $\mu$: viscosity [Pa·s] of fluid $U_x$: flow velocity average value [m/s] at each space pixel at cross-section at distance x $\rho$: density of fluid [kg/m³]

k: constant

With the microstructure analysis method according to an embodiment of the present invention performing the above-described fluid analysis, in the step (a), fluid analysis may be performed regarding a case of inflow of a fluid from a predetermined inflow face of the porous body, and deriving at least flow velocity for each space pixel as the information relating to flow; and in the step (b), the microstructure of the porous body may be analyzed by deriving through-flow volume Q of the fluid per unit time at the each placed virtual curved surface solid, based on the information relating to the placed virtual, curved surface solids and the flow velocity for each space pixel, and deriving flow-through velocity T of each virtual curved surface solid by T=Q/($\pi d^2/4$) based on the derived through-flow volume Q and an equivalent diameter d of the virtual curved surface solid (=6× volume V of virtual curved surface solid/surface area S of virtual curved surface solid). In this case, in the step (b), the microstructure of the porous body may be analyzed by classifying the virtual curved surface solids of which the derived flow-through velocity T is included in a low-flow-velocity as low-flow-velocity curved surface solids, or the microstructure of the porous body may be analyzed by classifying the virtual curved surface solids of which the derived flow-through velocity T is included in a high-flow-velocity as high-flow-velocity curved surface solids. Also, in the step (b), the microstructure of the porous body may be analyzed by classifying the virtual curved surface solids into low-flow-velocity curved surface solids, mid-flow-velocity curved surface solids, and high-flow-velocity curved surface solids, based on the magnitude of the value of the derived flow-through velocity T. Now, there are cases where pores of a porous body simulated with virtual curved surface solids of which the flow-through velocity T is small may not contribute much to transmittance of the fluid, leading increased pressure drop, and deterioration in thermal conductivity and thermal capacity of the material. Also, there are cases where pores of a porous body simulated with virtual curved surface solids of which the flow-through velocity T is great, exhibit great flow resistance when the fluid passes through, or the fluid may pass through in a short time and the pores do not contribute much to collecting performance. Accordingly, classifying a part of the virtual curved surface solids as low-flow-velocity curved surface solids with small flow-through velocity T and high-flow-velocity curved surface solids with great flow-through velocity T in this way enables the microstructure of the porous body to be analyzed with good precision. In this case, in the step (b), a flow velocity ratio $T_f (=T/T_{in})$ of the derived flow-through velocity T and an average flow velocity $T_{in}$ of the fluid at the inflow face in the fluid analysis may be derived, the classification is performed such that, of the placed virtual curved surface solids, virtual curved surface solids where $T_f<2$ are classified as the low-flow-velocity curved surface solids, virtual curved surface solids where $2 \leq T_f < 8$ as the mid-flow-velocity curved surface solids, and virtual curved surface solids where $8 \leq T_f$ as the high-flow-velocity curved surface solids. Performing classification using the flow velocity ratio $T_f$ in this way enables the microstructure of the porous body to be analyzed more precisely. Also, in the step (b), the performance of the porous body may be determined to be acceptable when the volume ratio of the low-flow-velocity curved surface solids in the multiple virtual curved surface solids is at or below a predetermined threshold. The predetermined threshold may be 20%, for example. Also, in the step (b), the performance of the porous body may be determined to be acceptable when the volume ratio of the high-flow-velocity curved surface solids in the multiple virtual curved surface solids is at or below a predetermined threshold. The predetermined threshold may be 10%, for example.

With the microstructure analysis method according to the present invention, in the step (b), the microstructure of the porous body may be analyzed by an equivalent diameter d of the placed virtual curved surface solids being derived by d=6×(volume V of virtual curved surface solid)/(surface area S of virtual curved surface solid). Thus, by deriving the equivalent diameter d of virtual curved surface solids as microstructure analysis enables the property of the pores of the porous body to be analyzed based on this equivalent diameter d, for example. In this case, with the step (b), the average value of the derived equivalent diameters d may be derived as the average pore diameter of the porous body. Also, in the step (b), the microstructure of the porous body may be analyzed by the virtual curved surface solids of which the derived equivalent diameter d is included in a predetermined small-diameter region being classified into small-diameter curved surface solids, or the microstructure of the porous body may be analyzed by the virtual curved surface solids of which the derived equivalent diameter d is included in a predetermined large-diameter region being classified into large-diameter curved surface solids. Further, in the step (b), the microstructure of the porous body may be analyzed by classifying the virtual curved surface solids into small-diameter curved surface solids, mid-diameter curved surface solids, and large-diameter curved surface solid, based on the magnitude of the value of the derived equivalent diameter d. Now, with pores of the porous body simulated with virtual curved surface solids of which the equivalent diameter d is small, there are cases where the flow velocity of the fluid passing through is small, leading to increased pressure drop, or cases where the catalyst applied to the walls of the pores to use the porous body as a filter may not be appropriately applied, or the like. Also, with pores of the porous body simulated with virtual curved surface solids of which the equivalent diameter d is great, there are cases where the flow velocity of the fluid passing through is great to the point of not contributing to collecting performance very much when using the porous body as a filter. Accordingly, classifying a part of the virtual curved surface solids as virtual curved surface solids with small equivalent diameter d and virtual curved surface solids with great equivalent diameter d in this way enables the microstructure of the porous body to be analyzed with good precision. In this case, in the step (b), the classification may be performed such that, of the placed virtual curved surface solids, virtual curved surface solids where d<10 µm are classified as the small-diameter curved surface solids, virtual curved surface solids where 10 µm≤d≤25 µm are classified as the mid-diameter curved surface solids, and virtual curved surface solids where 25 µm<d are classified as the large-diameter curved surface solids. Also, in the step (b) the performance of the porous body may be determined to be acceptable when the volume ratio of the mid-diameter curved surface solid in the multiple virtual curved surface solids is at or above a predetermined threshold. The predetermined threshold may be 60%, for example, or may be 70%.

A program according to the present invention is to cause one or multiple computers to realize the steps of the microstructure analysis method of the present invention according to any one of the above-described embodiments. The program may be recorded in a computer-readable recording medium (e.g., hard disk, ROM, FD, DC, DVD, etc.), or may be transmitted from a certain computer to another computer via a transmission medium (communication network such as the Internet or a LAN), or may be exchanged by any other form. Executing this program by one computer or sharing the steps among multiple computers to be executed executes the steps of the above-described microstructure analysis method, whereby advantages the same as with the microstructure analysis method can be obtained.

A microstructure analysis device according to the present invention includes:

a storage unit configured to store porous body data in which is correlated position information representing position of a pixel obtained by a 3 dimensional scan of a porous body, and pixel type information representing whether a space pixel representing that the pixel is space or a matter pixel representing that the pixel is matter;

a virtual curved surface solid placing unit configured to take a curved surface solid including a parent virtual sphere and one or more child virtual spheres with which a portion of pixels occupied by the parent virtual sphere overlap as a virtual curved surface solid, and place the multiple virtual curved surface solids so as to fill in the space pixels with curved surface solid pixels which are pixels occupied by the virtual curved surface solids, referencing the porous body data; and a microstructure analyzing unit configured to analyze the microstructure of the porous body based on information relating to the placed virtual curved surface solids.

This microstructure analysis device places multiple curved surface solids including a parent virtual sphere and one or more child virtual spheres partially overlapping pixels occupied by the parent virtual sphere to fill in space pixels with curved surface solid pixels which are pixels occupied by the virtual curved surface solids, referencing the porous body data, and analyzes the microstructure of the porous body based on information relating to the placed virtual curved surface solids. Thus, space (pores) having complicated shapes within the porous body are replaced with virtual curved surface solids of shapes having multiple spheres combined, so space within a porous body can be better simulated as a group of multiple virtual curved surface solids. Being based on information relating to the virtual curved surface solids enables the microstructure of the porous body to be analyzed more precisely. Note that the microstructure analysis device according to the present invention may have operations of the means added or other means added, so as to realize the steps of any of the microstructure analysis methods described above.

DETAILED DESCRIPTION OF THE INVENTION

Next, an embodiment of the present invention will be described with reference to the drawings.

Figure 1:
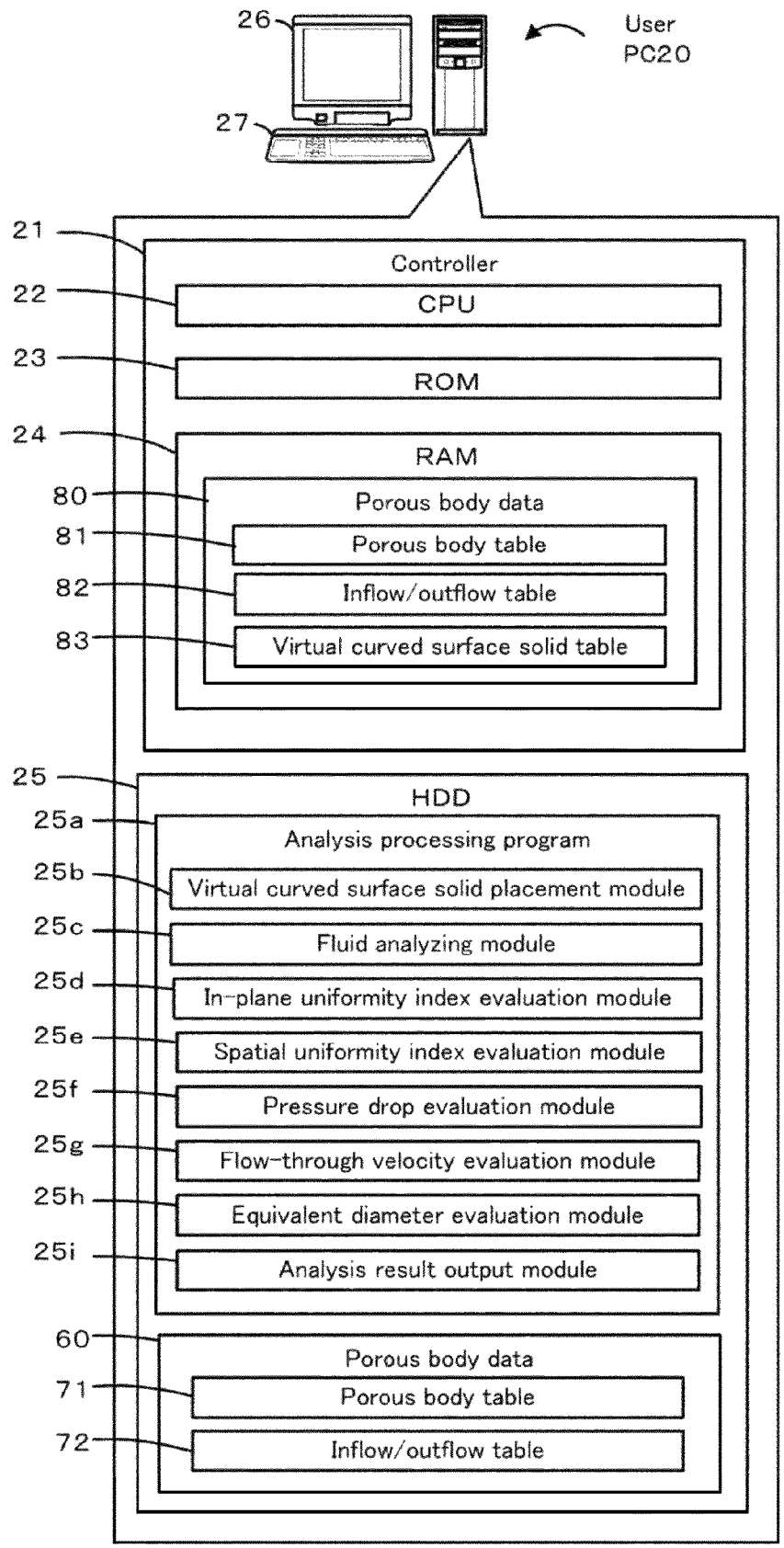
FIG. 1 is a configuration diagram of a user personal computer 20 according to the present embodiment.

FIG. 1 is a configuration diagram schematically illustrating the configuration of a user personal computer (PC) 20 which is an embodiment of the microstructure analysis device according to the present invention. This user PC 20 has a controller 21 including a CPU 22 which executes various types of processing, ROM 23 which stores various types of processing programs and so forth, RAM 24 which temporarily stores data, and so forth, and an HDD 25, which is large-capacity memory, to store various types of data such as various types of processing programs such as an analysis processing program 25a and porous body data 60 which is 3-dimensional pixel data of porous body and so forth. Note that the PC 20 has a display 26 for displaying various types of information on a screen, and an input device 27 such as a keyboard for a user to input various types of commands. The porous body data 60 stored in the HDD 25 includes a porous body table 71 and an inflow/outflow table 72, whereby the user PC 20 can analyze microstructures of porous body based on the porous body data 60 stored in the HDD 25, which will be described later. Also, in the process of analyzing microstructures, the RAM 24 stores porous body data 80. The porous body data 80 includes a porous body table 81, an inflow/outflow table 82, and a virtual curved surface solid table 83, which will be described in detail later.

Figure 2:
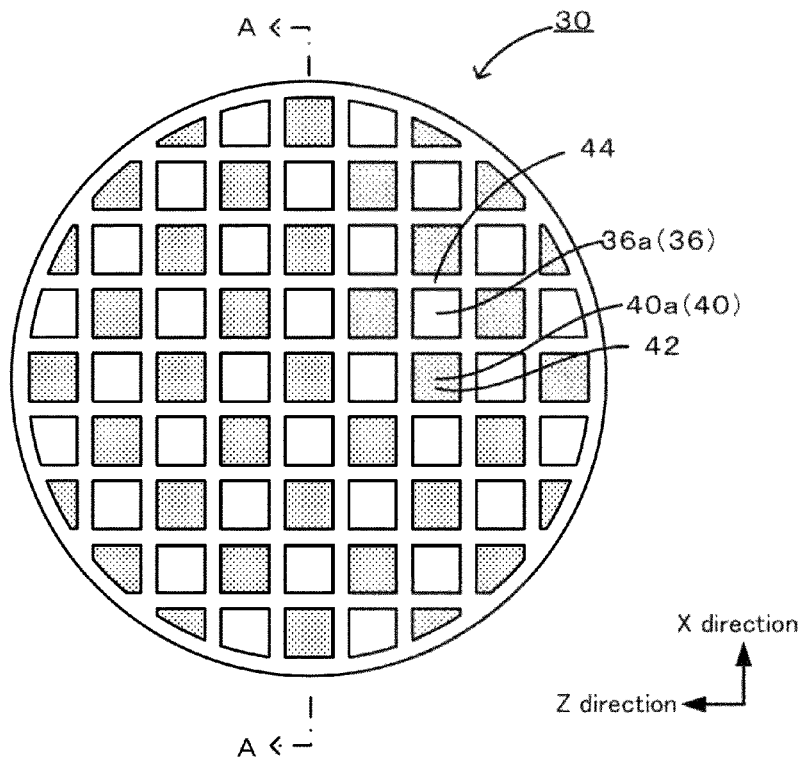
FIG. 2 is a frontal diagram of the honeycomb filter 30 including the porous body partition 44.
Figure 3:
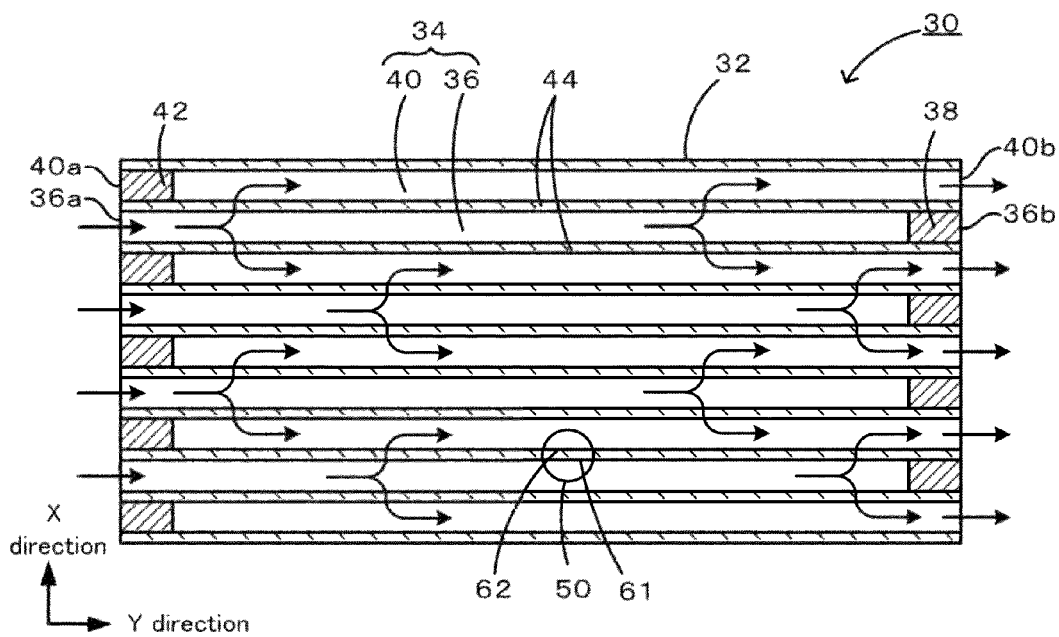
FIG. 3 is a cross-sectional view taken along A-A in FIG. 2.

Now, the porous body which the user PC 20 analyzes will be described. FIG. 2 is a frontal view of a honeycomb filter 30 including a porous body partition 44 which is a porous body, and FIG. 3 is a cross-sectional diagram taken along line A-A in FIG. 2.

the honeycomb filter 30 is a diesel particulate filter (DPF) having a function of filtering particulate matter (PM) in exhaust fumes from a diesel engine. This honeycomb filter 30 has multiple cells 34 (see FIG. 3) sectioned by porous partitions 44, with an external protective portion 32 formed on the perimeter thereof. A ceramic material such as Si-bonded SiC, Cordierite, or the like is preferably used for the porous partition 44, from the perspective of strength and heat resistance. The thickness of the porous partition 44 is preferably 200 µm to less than 600 µm, and is 300 µm with the present embodiment. The porous partition 44 has an average pore diameter (by mercury intrusion technique) of 10 µm to less than 60 µm, and porosity (voidage) of 40% to less than 65%. The great number of cells 34 formed in the honeycomb filter 30 include inlet-opened cells 36 of which the inlet 36a is open and the outlet 36b has been sealed by an outlet sealant 38, and outlet-opened cells 40 of which an inlet 40a is sealed by an inlet sealant 42 and an outlet 40b is open, as illustrated in FIG. 3. These inlet-opened cells 36 and outlet-opened cells 40 are arrayed so as to be alternatingly adjacent. Cell density is, for example, 15 cells/cm² to less than 65 cells/cm². The external protective portion 32 is a layer for protecting the outer periphery of the honeycomb filter 30, and may include the above-described inorganic particles, aluminosilicate, alumina, silica, zirconia, ceria, mullite, and like inorganic fibers, and colloidal silica, clay, and like bonding materials.

This honeycomb filter 30 is installed downstream of a diesel engine not illustrated in the drawings, for example, and is used to purge exhaust gas including PM so as to be discharged into the atmosphere. Note that the arrow in FIG. 3 illustrates the flow of exhaust gas at this time. The exhaust gas including PM from the diesel engine flows into inlet-opened cells 36 from the inlets 36a of the honeycomb filter 30, and then flows into adjacent outlet-opened cells 40 through the porous partitions 44, so as to be discharged from the outlets 40b of the outlet-opened cells 40 into the atmosphere. The PM is collected as the exhaust gas including PM flows through the porous partitions 44 from the inlet-opened cells 36 to the outlet-opened cells 40, the exhaust gas which flowing into the outlet-opened cells 40 is thus clean exhaust gas not including PM. The insides of the pores in the porous partition 44 are coated with an oxidation catalyst such as platinum or the like, which is not illustrated in the drawings, which oxidizes the collected PM so as to prevent deterioration in porosity of the porous body partition 44 and sudden increase in pressure drop.

A green body or slurry prepared by mixing a substrate with a pore-forming agent and dispersant can be used as a material to fabricate the honeycomb filter 30. The ceramic material described above can be used for the substrate. For example, a mixture of 80:20 by mass of Sic powder and metal Si powder can be used for a substrate of SiC. The pore-forming agent preferably burns away in the later firing, examples thereof including starch, coke, foamed resin, or the like. A surfactant such as ethylene glycol or the like can be used for the dispersant. The means for preparing the green body are not restricted in particular, examples thereof including methods using a kneader, a vacuum kneading machine, and so forth. This green body is formed by extrusion into the shaft illustrated in FIGS. 2 and 3 using a mold with cells 34 arrayed, and the cells 34 sealed off by the outlet sealant 38 and inlet sealant 42, for example, and then dried, pre-fired, and fired, whereby the honeycomb filter 30 including the porous partitions 44 can be fabricated. The outlet sealant 38 and inlet sealant 42 may be formed of the material used to form the porous partitions 44. The pre-firing process is to burn away organic components included in the honeycomb filter 30, at a temperature lower than the firing temperature. The firing temperature can be 1400° C. to 1450° C. with cordierite material, and 1450° C. with Si-bonded SiC. The honeycomb filter 30 including the porous partitions 44 is obtained through such processes.

The HDD 25 of the user PC 20 stores 3-dimensional pixel data of the porous partitions 44 obtained by performing a CT scan on this honeycomb filter 30, as porous body data 60. With the present embodiment, an X-Y plane indicated by the X direction and Y direction in FIG. 3 is the cross-sectional plane of photography, along which a CT scan is taken by multiple images being shot in the Z direction in FIG. 2, thereby obtaining pixel data. With the present embodiment, the resolution in each of the X, Y, and Z directions is 1.2 μm, so a cube 1.2 μm in all dimensions is the smallest unit of the 3-dimensional pixel data, i.e., a pixel. The resolution in each of the X, Y, and Z directions may be set as appropriate, depending on the performance of the CT imaging device, the size of the particles to be analyzed, and so forth. Also, the resolution may be of different values in each direction. While not restrictive in particular, the resolution in each of the X, Y, and Z directions may be set to any value within a range of, for example, 0.5 μm to 3.0 μm. Note that the higher the resolution is (the smaller the length of the pixels in each of the X, Y, and Z directions is), the higher the precision of analysis is. From the perspective of precision of the analysis, the resolution in each of the X, Y, and Z directions is preferably 3.0 μm or smaller. Also, the higher the resolution is, the longer the analysis time (calculation time) becomes, but the resolution in each of the X, Y, and Z directions may be set to be smaller than 0.5 μm. For example, this may be 0.2 μm to 0.3 μm, or even smaller than 0.2 μm. The position of each pixel is expressed by XYZ coordinates (the coordinate value 1 corresponds to 1.2 μm, which is the length of each side of a pixel), and type information determining whether or not that pixel is space (pore) or object (constituent material of porous partition 44) is added thereto, and stored in the HDD 25. With the present embodiment, a value 0 is added as type information for pixels representing space (space pixels), and a value 9 is added as type information for pixels representing matter (matter pixels). Note that in reality, the data obtained by the CT scan is luminance data for each XYZ coordinate, for example. The porous body data 60 used with the present embodiment can be obtained by binarizing this luminance data at a predetermined threshold to determine whether a space pixel or matter pixel, for each coordinate. The predetermined threshold is a value set as a value capable of suitably distinguishing between space pixels and matter pixels. This threshold may be determined by experiment beforehand, so that the porosity of the porous partition 44 obtained by measurement, and the porosity in the pixel data after binarization, are approximately equal. This CT scan can be performed using an SMX-160CT-SV3, manufactured by Shimadzu Corporation, for example.

Figure 4:
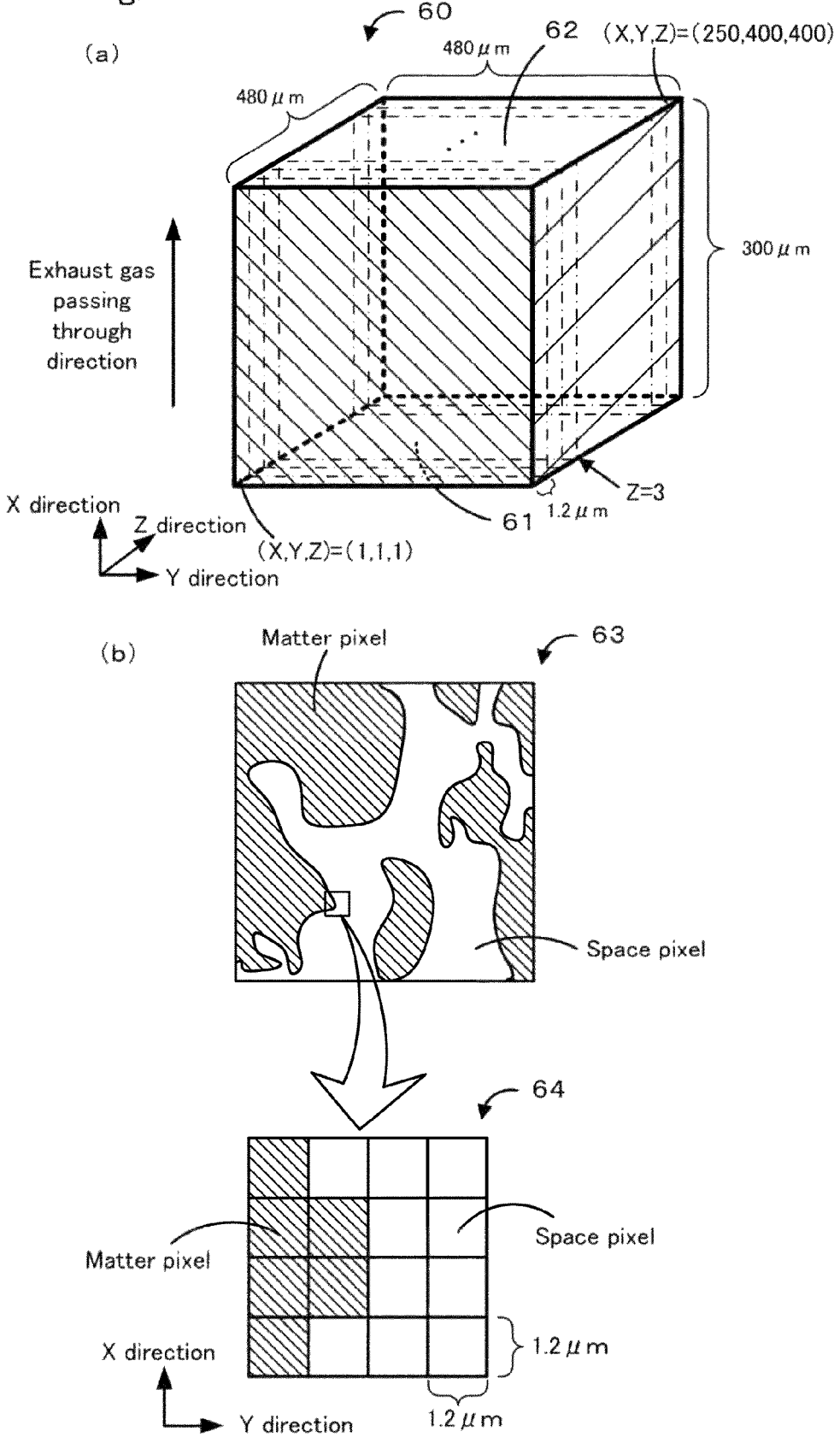
FIG. 4 is a conceptual diagram of porous body data 60.
Figure 5:
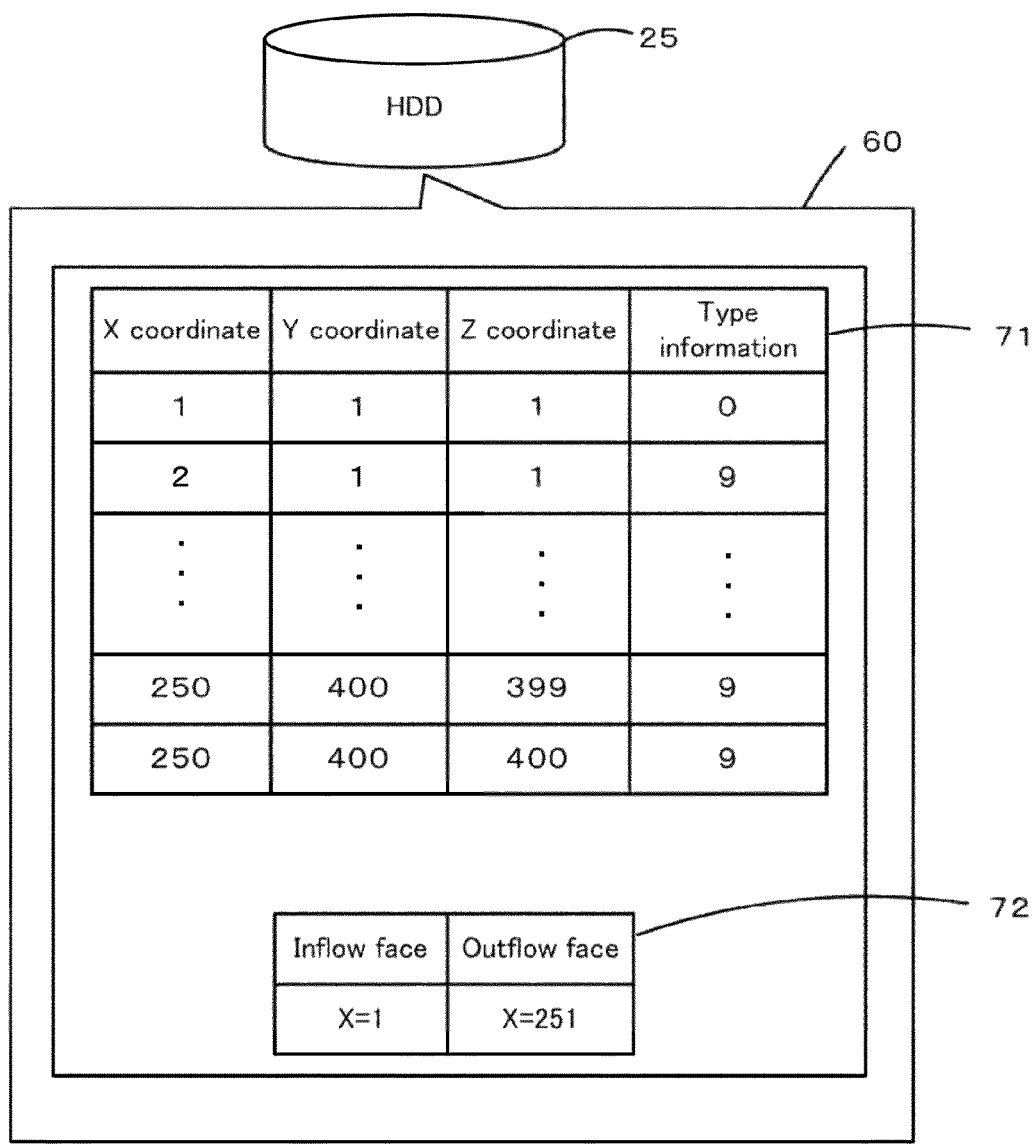
FIG. 5 is an explanatory diagram of porous body data 60.

FIG. 4 is a conceptual diagram of the porous body data 60. FIG. 4(a) is a conceptual diagram of the porous body data 60 obtained as pixel data by performing a CT scan of the porous partition 44 in region 50 in FIG. 3. With the present embodiment, this porous body data 60 is extraction of pixel data of a cuboid portion from the pixel data of the porous partition 44, of a cuboid 300 μm (=1.2 μm×250 pixels) which is the same value as the thickness of the porous partition 44 in the direction of exhaust gas passing through, in the X direction, 480 μm (=1.2 μm×400 pixels) in the Y direction, and 480 μm (=1.2 μm×400 pixels) in the Z direction. The later-described analysis processing is performed on this porous body data 60. The size of the porous body data 60 can be set as appropriate depending on the thickness and size of the porous partition 44, allowable calculation load, and so forth. For example, the length in the X direction is not restricted to 300 μm and may be any value, as long as the same value as the thickness of the porous partition 44 in the direction of exhaust gas passing through. Also, while this is preferably the same value as the thickness of the porous partition 44 in the direction of exhaust gas passing through, it does not have to be the same value. The lengths in the Y direction and Z direction also are not restricted to 480 μm and may be other values, and the length in the Y direction and the Z direction may be different. Two faces of the six faces of the cuboid porous body data 60 (faces parallel to the Y-Z plane) are an inflow face 61 (see FIG. 3) which is the boundary face between the porous partition 44 and inlet-opened cell 36, and an outflow face 62 (see FIG. 3) which is the boundary face between the porous partition 44 and outlet-opened cell 40 in the region 50, and the remaining four faces are cross-sections of the porous partition 44. FIG. 4(b) is the X-Y plane (photography cross-section) 63 at the position in the porous body data 60 where the Z coordinate is value 3, and an enlarged diagram 64 of a part thereof. As illustrated in the enlarged diagram 64, the X-Y plane 63 is configured of an array of pixels of which each side is 1.2 μm, with each pixel being represented as being either a space pixel or a matter pixel. Note that while the photographed cross-section obtained by the CT scan is planar data with no thickness in the Z direction as illustrated in FIG. 4(b), each photographed cross-section is handled as having the thickness of the intervals between photographed cross-sections in the Z direction (1.2 µm), i.e., as each pixel being a cube of which each side is 1.2 µm, as described above. Note that the porous body data 60 is stored in the HDD 25 as data including a porous body table 71 correlating the XYZ coordinates serving as position information for each pixel with the type information, and an inflow/outflow table 72 representing the inflow face 61 and outflow face 62, as illustrated in FIG. 5. In FIG. 5, the "X=1" in the inflow/outflow table 72 means the plane X=1 on the XYZ coordinate system, and represents the inflow face 61 illustrated in FIG. 4(*a*). "X=251" represents the outflow face 62 in the same way. The HDD 25 also stores, besides this porous body data 60, many other porous body data 60 representing pixel data of the porous partition 44 other than the region 50 described above.

The analysis processing program 25*a* includes a virtual curved surface solid placement module 25*b*, a fluid analyzing module 25*c*, an in-plane uniformity evaluation module 25*d*, a spatial uniformity index evaluation module 25*e*, a pressure drop evaluation module 25*f*, a flow-through velocity evaluation module 25*g*, an equivalent diameter evaluation module 25*h*, and an analysis result output module 25*i*. The virtual curved surface solid placement module 25*b* has a function of referencing the porous body data 80, taking a curved surface solid including a parent virtual sphere and one or more child virtual spheres partially overlapping the parent virtual sphere with regard to occupied pixels, as a virtual curved surface solid, and placing multiple virtual curved surface solids so as to fill in space pixels with curved surface solid pixels which are pixels occupied by virtual curved surface solids. The fluid analyzing module 25*c* has a function of deriving information relating to the flow of fluid for each space pixel at the time of the fluid passing through the interior of the porous body, by performing fluid analysis based on the porous body data 80. The in-plane uniformity index evaluation module 25*d* has a function of deriving one or more in-plane uniformity index $\gamma_x$ of flow velocity at a cross-section parallel to the inflow face 61 of the porous body data 80, based on information relating to the virtual curved surface solid placed by the virtual curved surface solid placement module 25*b* and information relating to flow that has been derived by the fluid analyzing module 25*c*, and evaluating the porous body based on the in-plane uniformity index $\gamma_x$. The spatial uniformity index evaluation module 25*e* has a function of deriving a spatial uniformity index $\gamma$ of the flow velocity at the porous body using the in-plane uniformity index $\gamma_x$ derived by the in-plane uniformity index evaluation module 25*d*, and evaluating the porous body based on the in-plane uniformity index $\gamma_x$. The pressure drop evaluation module 25*f* has functions of deriving pressure drop P per unit thickness of the porous body using the in-plane uniformity index $\gamma_x$ derived by the in-plane uniformity index evaluation module 25*d*, and evaluating the porous body based on the pressure drop P. The flow-through velocity evaluation module 25*g* has functions of deriving flow-through velocity T and flow velocity ratio $T_f$ for each virtual curved surface solid, based on information relating to position of virtual curved surface solids placed by the virtual curved surface solid placement module 25*b* and information relating to the flow derived by the fluid analyzing module 25*c*, classifying the virtual curved surface solids based on the flow-through velocity T and flow velocity ratio $T_f$, and evaluating the porous body based on the classification results. The equivalent diameter evaluation module 25*h* has functions of deriving equivalent diameter d for the virtual curved surface solids placed by the virtual curved surface solid placement module 25*b*, classifying the virtual curved surface solids based on the equivalent diameter d, and evaluating the porous body based on the classification results. The analysis result output module 25*i* has a function of compiling the various types of values and evaluation results and so forth that have been derived, and outputting to be stored in the HDD 25 as analysis result data. The controller 21 executing the analysis processing program 25*a* realizes the above-described functions of the virtual curved surface solid placement module 25*b*, fluid analyzing module 25*c*, in-plane uniformity evaluation module 25*d*, spatial uniformity index evaluation module 25*e*, pressure drop evaluation module 25*f*, flow-through velocity evaluation module 25*g*, equivalent diameter evaluation module 25*h*, and analysis result output module 25*i*.

Figure 6:
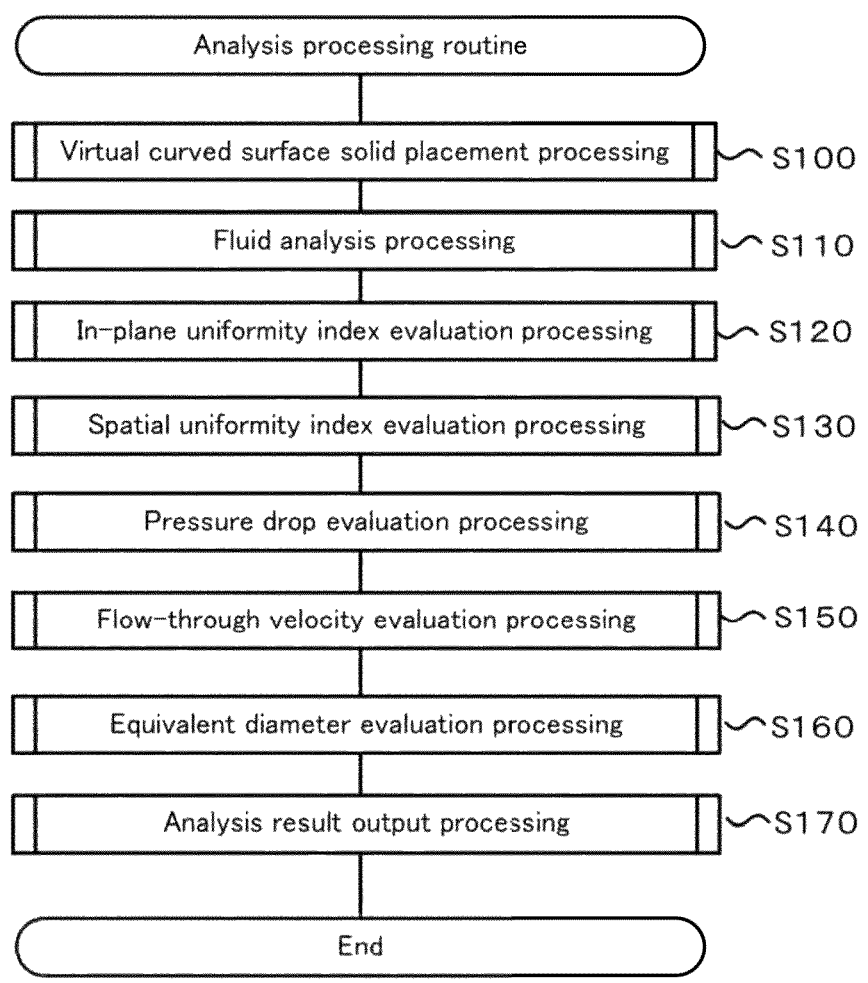
FIG. 6 is a flowchart illustrating an example of an analysis processing routine.

Next, the analysis processing which the user PC 20 performs with regard to the porous body data 60 will be described. FIG. 6 is a flowchart of an analysis processing routine. This analysis processing routine is carried out by the CPU 22 executing the analysis processing program 25*a* stored in the ROM 23 upon the user giving an instruction via the input device 27 to perform analysis processing. Note that while a case of performing analysis processing on the porous body data 60 will be described hereinafter, analysis processing can be performed on other porous body data in the same way. Which porous body data is to be analyzed may be determined beforehand, or may be specified by the user.

Upon the analysis processing routine being executed, the CPU 22 first executes curved surface solid placement processing, which is processing to place virtual curved surface solids so as to fill in space pixels in the porous body data 60 (step S100).

Figure 7:
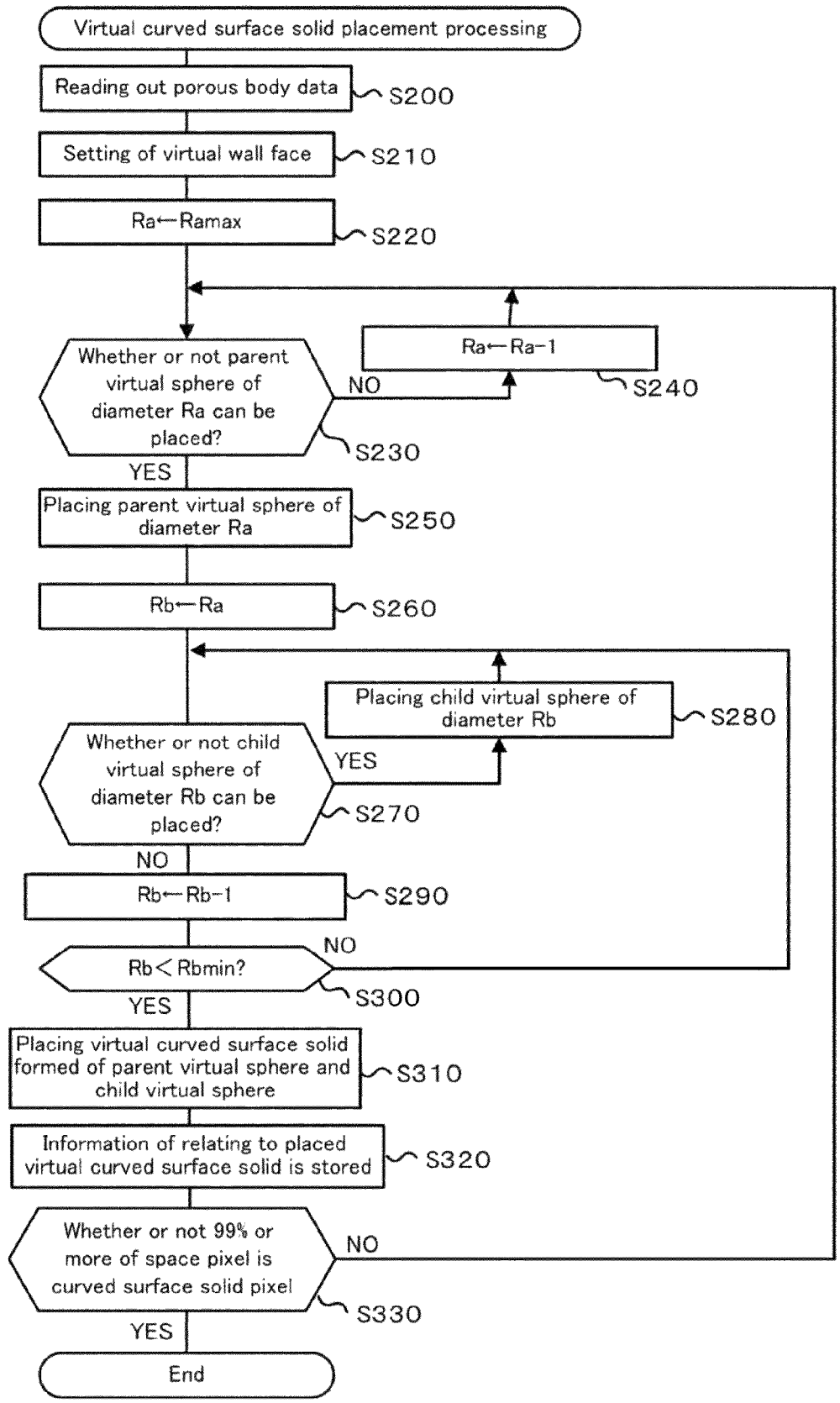
FIG. 7 is a flowchart illustrating an example of virtual curved surface solid placement processing.

Now, we will depart from description of the analysis processing routine to describe the virtual curved surface solid placement processing. FIG. 7 is a flowchart of the virtual curved surface solid placement processing. This virtual curved surface solid placement processing is performed by the virtual curved surface solid placement module 25*b*. Upon the virtual curved surface solid placement processing being executed, the virtual curved surface solid placement module 25*b* first reads out the porous body data 60 stored in the HDD 25 and stores this in the RAM 24 (step S200). Thus, the same data as the porous body data 60 including the porous body table 71 and inflow/outflow table 72 stored in the HDD 25 is stored in the RAM 24 as the porous body data 80 including the porous body table 81 and inflow/outflow table 82. Setting of virtual wall faces is performed regarding the porous body data 80 that has been read out (step S210). Specifically, based on the porous body data 80 which is a cuboid 300 µm×480 µm×480 µm, the user specifies the distance therefrom to a virtual wall face covering the periphery thereof by way of the input device 27, which the virtual curved surface solid placement module 25*b* accepts and stores in the RAM 24. For example, if the distance to the virtual wall face is specified as being 1 µm, the virtual curved surface solid placement module 25*b* presumes that there is a virtual wall face 1 µm on the outer side of each face of the porous body data 80 in the X, Y, and Z directions, and that the outer side thereof has all matter pixels placed thereat. That is to say, the porous body data 80 is a 300 µm×480 µm×480 µm cuboid, so this is presumed to be covered with a cuboid virtual wall face that is 302 µm×482 µm×482 µm. This virtual wall is set to restrict regions where virtual curved surface solids (parent virtual spheres and child virtual spheres) described later can be placed.

Next, the virtual curved surface solid placement module 25*b* sets a maximum value Ramax for the diameter Ra of the parent virtual sphere (step S220), and determines whether or not a parent virtual sphere of diameter Ra can be placed in the space pixels on the inner side of the virtual wall face set in step S210 (step S230). A parent virtual sphere with a diameter Ra is a virtual sphere having a size of a diameter of Ra (µm), with the center thereof at the center of one of the pixels. Whether or not this parent virtual sphere of diameter Ra can be placed is determined as follows, for example. First, any one pixel of space pixels (pixels of which the type information is value 0) at that point-in-time is selected. In the event that placing the parent virtual sphere of diameter Ra centered on the selected pixel causes the parent virtual sphere to overlap with a matter pixel or a virtual curved surface solid already placed, another space pixel is selected again as the center. One space pixel after another is selected, and in the event that the parent virtual sphere does not overlap a matter pixel or a virtual curved surface solid already placed, determination is made that the parent virtual sphere of diameter Ra can be placed at that position. Also, in the event that the parent virtual sphere overlaps a matter pixel or a virtual curved surface solid already placed regardless of every space pixel being selected as the center at that point-in-time, determination is made that the parent virtual sphere of diameter Ra cannot be placed. Note that the order of selecting pixels to serve as a center may be random, or may be performed in order from pixels on the inflow face 61 toward pixels on the outflow face 62. Also, the value of the maximum value Ramax may be any value as long as a value equal to or greater than the maximum value of the diameter of pores normally present in the porous partition 44, and for example, the value can be set by reference to a value obtained beforehand by experiment. Upon determining in step S230 that the parent virtual sphere cannot be placed, the diameter R is decremented by 1 (step S240), and the processing of step S230 and thereafter is performed. Note that while the decremented value is 1 with the present embodiment, this may be set as appropriate according to the allowable calculation load and so forth.

In the event that determination is made in step S230 that the parent virtual sphere can be placed, one parent virtual sphere of diameter Ra is placed at that position (step S250). Specifically, the type information corresponding to the pixel occupied by the parent virtual sphere when the parent virtual sphere of diameter Ra is placed, in the porous body table 71 of the porous body data 80 stored in the RAM 24 in step S200, is updated to a value 3, representing the pixel occupied by a parent virtual sphere. Note that while the type information of a pixel of which the center is included in the parent virtual sphere is updated to the value 3 with the present embodiment, the type information of the pixel may be updated to a value 3 when a predetermined percentage of the volume of the pixel (e.g., 50%) or more is occupied by the parent virtual sphere, just type information of pixels completely included in the parent virtual sphere may be updated to a value 3, or the type information of the pixel may be updated to a value 3 when even a part of the pixel is occupied by the parent virtual sphere. This holds true for pixels occupied by later-described child virtual spheres as well.

Next, the virtual curved surface solid placement module 25b sets a diameter Rb of a child virtual sphere to the same value as the diameter Ra (step S260), and determines whether or not a child virtual sphere of a diameter Rb can be placed in the space pixels on the inner side of the virtual wall face set in step S210 (step S270). A child virtual sphere with a diameter Rb is a virtual sphere having a size of a diameter of Rb (µm), with the center thereof at the center of one of the pixels, and with a part of the occupied pixels overlapping those of the parent virtual sphere. Also, the placement of the child virtual spheres is performed such that the center of the child virtual sphere overlaps the parent virtual sphere placed in step S250. Determination of whether or not this child virtual sphere of a diameter Rb can be placed is performed as follows, for example. First, any one pixel of pixels which the parent virtual sphere occupies at that point-in-time (a pixel with a type information value is 3) is selected. In the event that placing the child virtual sphere of diameter Rb centered on the selected pixel causes the child virtual sphere to overlap with a matter pixel or a virtual curved surface solid already placed, another pixel occupied by the parent virtual sphere is selected again as the center. One pixel after another is selected, and in the event that the child virtual sphere does not overlap a matter pixel or a virtual curved surface solid already placed, determination is made that the child virtual sphere of diameter Rb can be placed at that position. Also, in the event that the child virtual sphere overlaps a matter pixel or a virtual curved surface solid already placed regardless of every pixel occupied by the parent virtual sphere being selected as the center at that point-in-time, determination is made that the child virtual sphere of diameter Rb cannot be placed.

In the event that determination is made in step S270 that the child virtual sphere can be placed, one child virtual sphere of diameter Rb is placed at that position (step S280). Specifically, of the porous body table 81 of the porous body data 80 stored in the RAM 24 in step S200, the type information corresponding to the pixel occupied by the child virtual sphere when the child virtual sphere of diameter Rb is placed is updated to a value 4, representing being occupied by a child virtual sphere. Note that no updating of type information is performed for pixels with type information of value 3, which are pixels occupied by the parent virtual sphere. That is to say, pixels where the parent virtual sphere and child virtual sphere overlap are correlated with the type information of the parent virtual sphere. Upon having placed one child virtual sphere, the processing of step S270 and thereafter is performed, step S280 is repeated and child virtual spheres of diameter Rb are placed, until determination is made that no child virtual sphere of diameter Rb can be placed. Note that mutual overlapping of child virtual spheres is permitted. That is to say, overlapping of pixels which one child virtual sphere occupies and pixels which another child virtual sphere occupies is permitted.

Upon determination being made in step S270 that no child virtual sphere can be placed, the diameter Rb is decremented by a value 1 (step S290), determination is made regarding whether or not the diameter Rb is smaller than the minimum value Rbmin (step S300), and if equal to or greater than the minimum value Rbmin, the processing of step S270 and thereafter is performed. The minimum value Rbmin is the lower limit value of the diameter Rb of the child virtual sphere, and is a threshold determined to prevent placement of child virtual spheres with relatively small diameters that would not affect the analysis results very much, for example. With the present embodiment, Rbmin is 2 µm.

In the event that the diameter Rb is smaller than the minimum value Rbmin in step S300, a virtual curved surface solid is formed of the parent virtual sphere placed in step S250 and child virtual spheres placed in step S280 (step S310). Specifically, of the porous body table 81 of the porous body data 80 stored in the RAM 24 in step S200, the type information corresponding to the pixels occupied by the parent virtual sphere (pixels of type information is value 3) and the pixels occupied by the child virtual sphere (pixels of type information is value 4) are updated to a value 5, representing being curved surface solid pixels occupied by the virtual curved surface solid. Also, an identification symbol of the virtual curved surface solid is correlated with the position information of the curved surface solid pixels updated to the value 5 this time. The identification symbol of the virtual curved surface solid is a value given to each virtual curved surface solid in accordance with the order of being placed, for example, and curved surface solid pixels configuring one virtual curved surface solid have the same identification symbol correlated therewith. Information relating to this virtual curved surface solid is stored in the RAM 24 (step S320), and determination is made regarding whether or not 99% or more of space pixels have been replaced with the curved surface solid (step S330). This determination is made specifically by referencing the type information of each pixel included in the porous body table 71 stored in the RAM 24, and determining whether or not the number of pixels of which the type information of value 5 is 99% or more of the total number of pixels, of the number of pixels of which the type information is of value 0 and the number of pixels of which the type information is of value 5. Note that the determination threshold is not restricted to 99%, and that other values may be used. In the event that determination is made in step S330 that less than 99% of space pixels have been replaced with the curved surface solid, processing of step SS230 and thereafter is performed, so as to situate the next virtual curved surface solid. On the other hand, in the event that determination is made in step S330 that 99% or more of space pixels have been replaced with the curved surface solid, the virtual curved surface solid placement processing ends.

Figure 8:
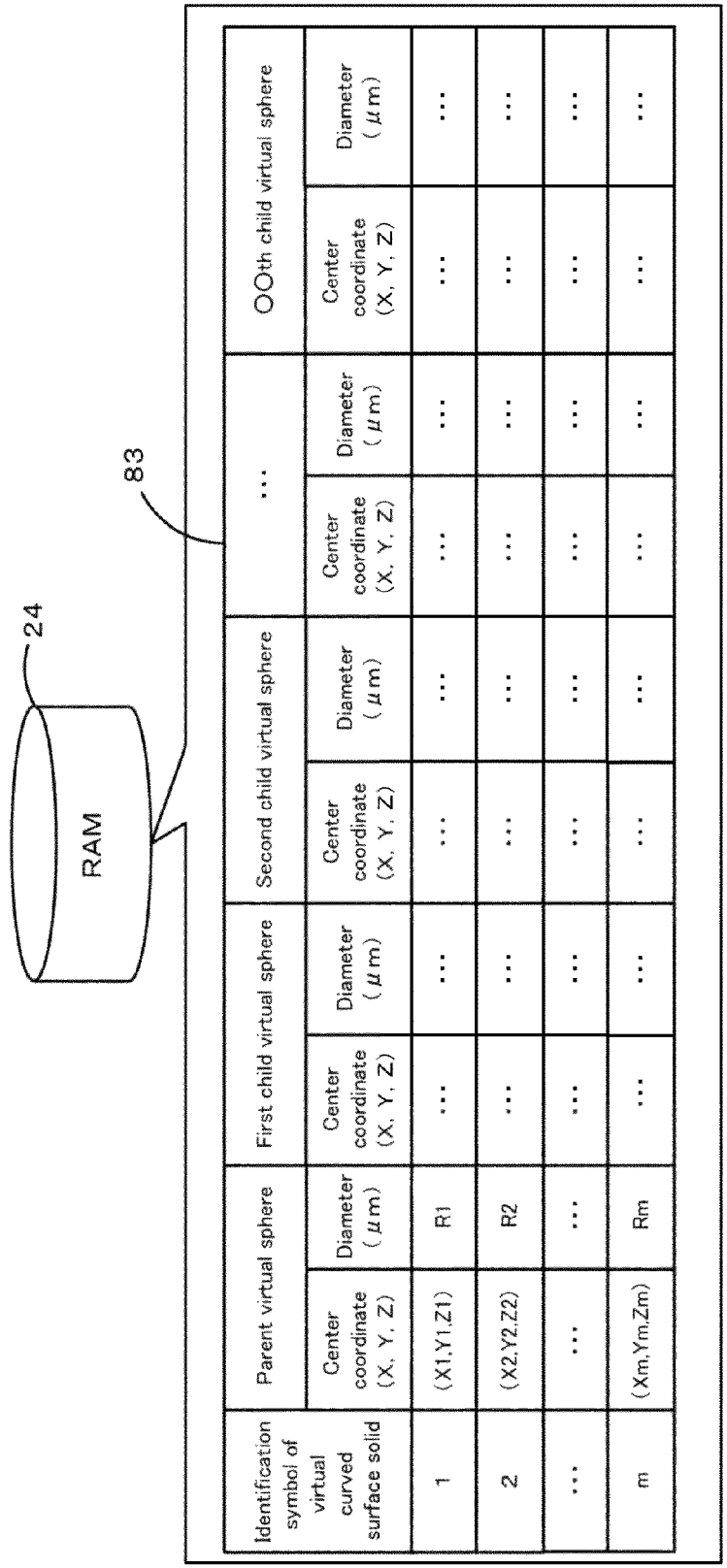
FIG. 8 is an explanatory diagram illustrating an example of a curved surface solid table 83.

Note that in step S320, a virtual curved surface solid table 83 in which are correlated an identification symbol identifying the virtual curved surface solid, the center coordinates (X, Y, Z) and diameter of the parent virtual sphere configuring the virtual curved surface solid, and the center coordinates and diameter of the one or more child virtual spheres configuring the virtual curved surface solid, is stored as information relating to the virtual curved surface solid in the RAM 24, as part of the porous body data 80. FIG. 8 illustrates an example of the virtual curved surface solid table 83. As illustrated in the drawing, the virtual curved surface solid table 83 has correlated therein for each of the multiple virtual curved surface solids placed by repeating steps S230 through S320, an identification symbol, the center coordinates and diameter of the parent virtual sphere, and the center coordinates and diameter of the one or more child virtual spheres configuring the virtual curved surface solid. Also, since there are cases where multiple child virtual spheres exist for a single virtual curved surface solid, information of multiple child virtual spheres is correlated in an identifiable manner, such as first child virtual sphere, second child virtual sphere . . ., in accordance with the order of placement, for example. Note that a virtual curved surface solid in which not a single child virtual sphere exists, i.e., a virtual curved surface solid configured of a parent virtual sphere alone, is allowable.

Figure 9:
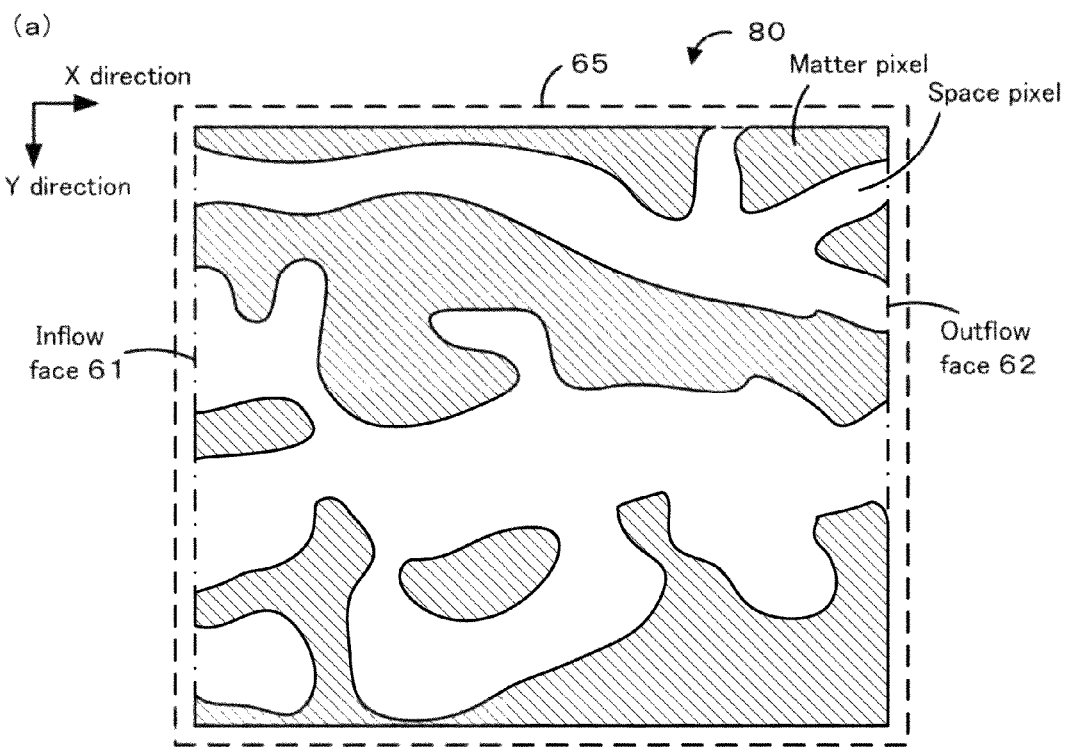
FIG. 9 is an explanatory diagram of placement of a parent virtual sphere.
Figure 9:
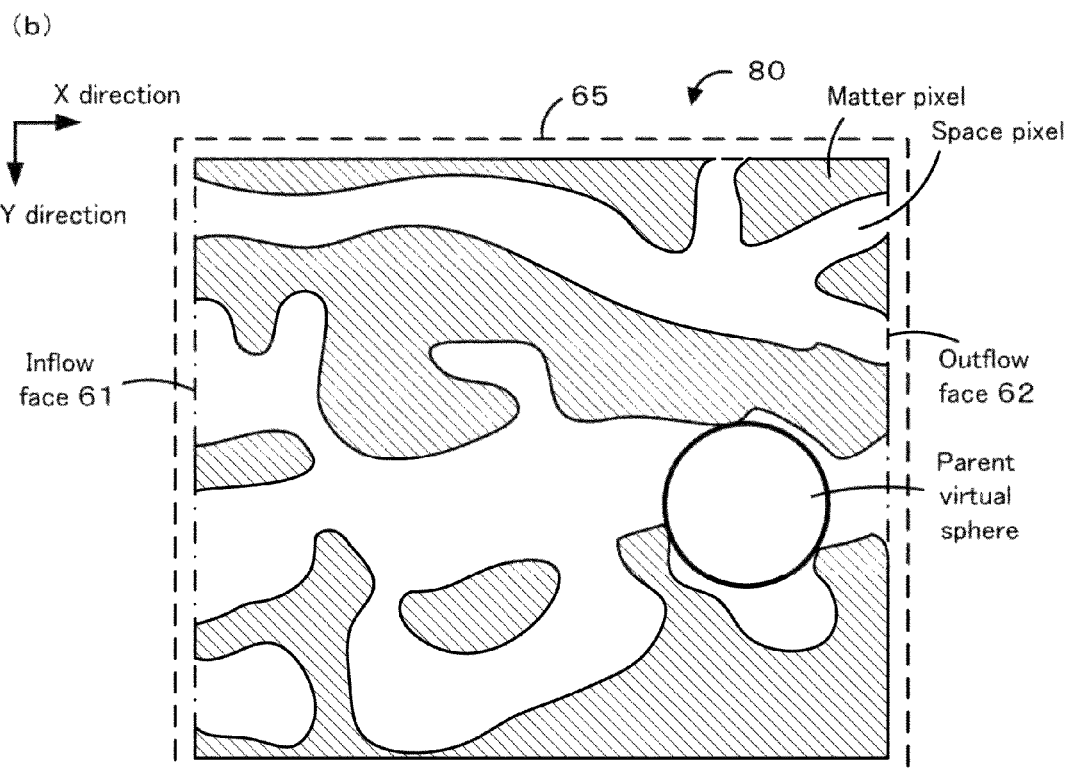
Figure 10:
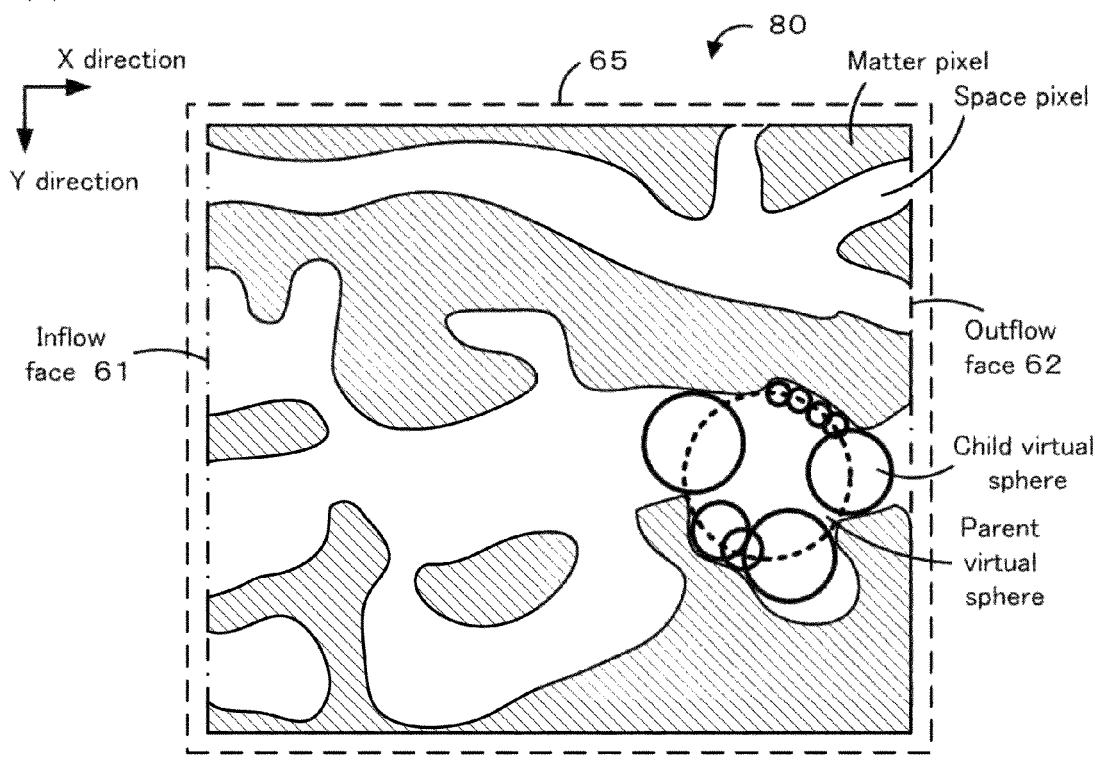
FIG. 10 is an explanatory diagram of placement of child virtual spheres and a virtual curved surface solid.
Figure 10:
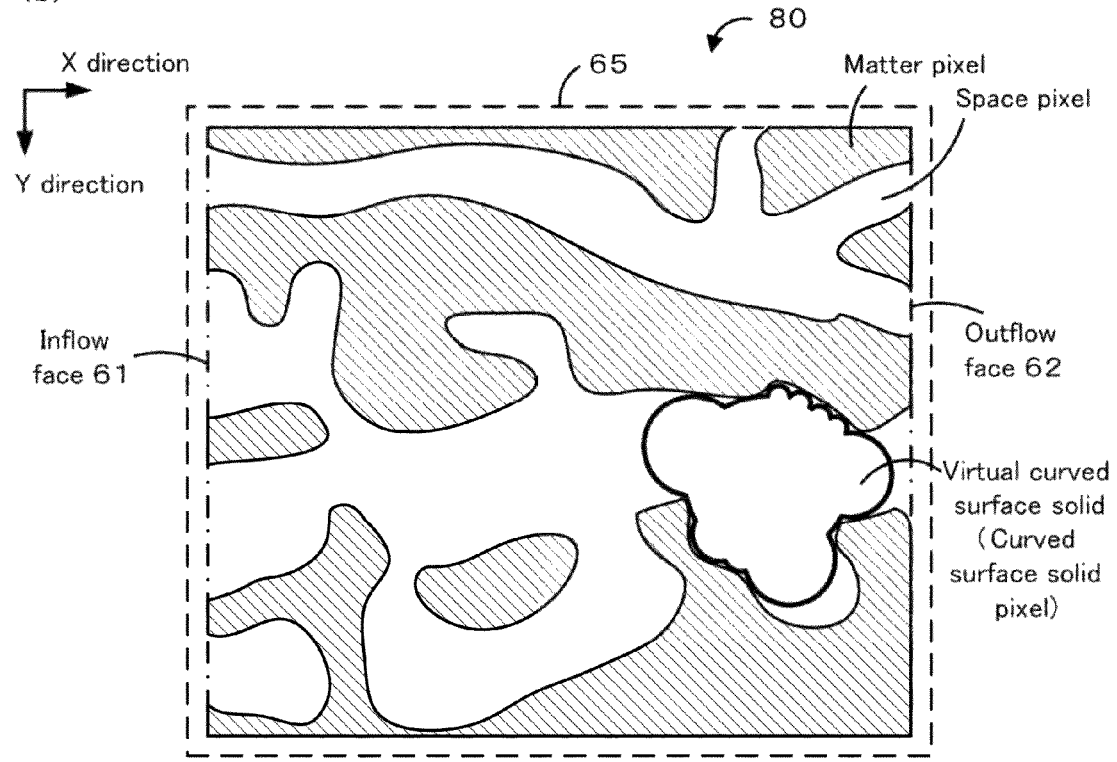

Due to this virtual curved surface solid placement processing, the virtual curved surface solid table 83 is stored in the RAM 24, and also the space pixels are replaced with curved surface solid pixels by the virtual curved surface solid that has been placed. Now, the way in which one virtual curved surface solid made up of a parent virtual sphere and child virtual spheres is placed by the virtual curved surface solid placing processing will be described. FIG. 9 is an explanatory diagram of placement of a parent virtual sphere, and FIG. 10 is an explanatory diagram of placement of child virtual spheres and a virtual curved surface solid. Note that FIGS. 9 and 10 illustrate, of the porous body data 80, the appearance of a cross-section parallel to the X direction, with placement of the virtual curved surface solid being illustrated two-dimensionally, to facilitate description. FIG. 9(a) is an explanatory diagram illustrating an example of the porous body data 80 immediately after having performed step S210, and before placing the virtual curved surface solid, and FIG. 9(b) is an explanatory diagram illustrating a state in which one parent virtual sphere has been placed. FIG. 10(a) is an explanatory diagram of a state where multiple child virtual spheres have been placed as to the parent virtual sphere that has been placed in FIG. 9(b). FIG. 10(b) is an explanatory diagram of a state where a virtual curved surface solid made up of the parent virtual sphere and child virtual spheres has been placed. As illustrated in FIG. 9(a), the porous body data 80 is made up of matter pixels and space pixels, with the inflow face 61, outflow face 62, and a virtual wall face 85 having been set. The virtual curved surface solid (parent virtual sphere, child virtual sphere) is placed so as to not extend outside from the virtual wall face 85. If the diameter Ramax is set to a sufficiently great value, performing the processing of steps S220 through S250 decrements the value of the diameter Ra by a value of 1 at a time, and when the greatest diameter which can be placed in the porous body data 80 in a range of not overlapping a matter pixel and not protruding outside from the virtual wall face 85, and the diameter Ra, are equal, one parent virtual sphere is placed (FIG. 9(b)). Next, steps S270 through S300 are repeated until the diameter Rb is determined in step S300 to be smaller than the minimum value Rbmin, whereby multiple child virtual spheres of various sizes of the diameter are placed so as to fill in the space pixels with the centers of the child virtual spheres overlapping the parent virtual sphere and also pixels which the child virtual spheres occupy not overlapping with matter pixels (FIG. 10(a)). Upon the diameter Rb being determined in step S300 to be smaller than the minimum value Rbmin, one virtual curved surface solid made up of the parent virtual sphere and the child virtual spheres placed so far is placed (FIG. 10(b)). The processing of steps S230 through S320 to place one virtual curved surface solid in this way is repeated until determination is made in step S330 that of the space pixels, the pixels replaced by curved surface solid pixels is 99% or more, whereby virtual curved surface solids are sequentially placed in other space pixels where a virtual curved surface solid is not yet placed, thereby filling up the space pixels with curved surface solid pixels. Thus, space (pores) having complicated shapes within the porous body are replaced with virtual curved surface solids of shapes having multiple spheres combined, so space within a porous body can be better simulated as a group of multiple virtual curved surface solids.

Let us return to the description of the analysis processing routine in FIG. 6. Upon the virtual curved surface solid placement processing of step S100 ending, the fluid analyzing module 25c performs fluid analysis processing to derive information relating to the flow of a fluid per space pixel at the time of a fluid passing through the interior of the porous body, by performing fluid analysis based on the porous body data 80 stored in the RAM 24 (step S110). This fluid analysis processing is performed by the lattice Boltzmann method. Specifically, fluid analysis is performed regarding a case of a fluid flowing in from the inflow face 61, where the centers of the pixels of the porous body data 80 are taken as the lattice points by the lattice Boltzmann method using a predetermined relational expression relating to the flow of fluid between each lattice point and adjacent lattice points. A flow vector made up of flow velocity and flow direction for each space pixel in the porous body data 80 is derived as information relating to the flow of the fluid at each space pixel, and the flow velocity vectors of each space pixel are stored in the porous body table 81 of the porous body data 80 in the RAM 24 in a correlated manner. Note that numerical values necessary of this fluid analysis, such as the average flow velocity $T_{in}$ of the fluid at the inflow face 61, viscosity $\mu$ of the fluid, density $\rho$ of the fluid, and so forth, are set in the analysis processing program 25a beforehand for example, and these numerical values are used to perform the analysis. These numerical values may be set by the user by way of the input device 27. Note that the average flow velocity $T_{in}$ is the average value of the flow velocity immediately prior to the fluid entering the porous body, and corresponds to the initial value of the flow velocity in fluid analysis. With the present embodiment, the average flow velocity $T_{in}$ is set to 0.01 m/s. Also, air of 0° C. and 1 atm is assumed for the fluid, with a viscosity $\mu$ of $1.73 \times 10^{-5}$ [Pa·s], and density $\rho$ of 1.25 [kg/m$^3$]. Note that the fluid analysis processing in step S110 does not take into consideration the virtual curved surface solid placed in step S100, and is performed as if curved surface solid pixels are also space pixels. While description has been made with the present embodiment that the fluid analysis processing in step S110 is performed based on the porous body data 80 stored in the RAM 24, this may be performed based on the porous body data 60 stored in the HDD 25.

Next, the in-plane uniformity index evaluation module 25d performs in-plane uniformity index evaluation where an in-plane uniformity index $\gamma_x$ is derived, and evaluates the porous body by performing acceptability evaluation based on the derived value (step S120). The in-plane uniformity index $\gamma_x$ is derived by deciding one cross-section parallel to the inflow face 61, and deriving from the following Expression (1) as a value at that cross-section. Note that an n number of average flow velocities $u_i$ at the cross-section described below, and cross-sectional area $A_i$ of each virtual curved surface solid within the cross-section, are derived as follows, for example. First, curved surface solid pixels included in a cross-section from which the in-plane uniformity index $\gamma_x$ is to be derived are identified based on a distance x between cross-section and the inflow face 61, and the position information and type information in the porous body table 81 stored in the RAM 24. Next how many types of identification symbols there are in virtual curved surface solids correlated with the identified curved surface solid pixels is counted, and this number is taken as the number n of virtual curved surface solids within the cross-section. Next, one of the identification symbols of the virtual curved surface solids within the cross-section is selected. Next, with regard to the curved surface solid pixel correlated with the selected identification symbol, i.e., the curved surface solid pixels configuring one virtual curved surface solid, the flow velocity vector correlated with each curved surface solid pixel in the fluid analysis processing is found, the average value of the flow velocity components in a direction perpendicular to the cross-section for each curved surface solid pixel is derived, and this is taken as average flow velocity $u_1$. Also, the number of pixels is counted for the curved surface solid pixels correlated with the selected identification symbol, and the product of the number of pixels and the area of the curved surface solid pixels following the cross-section (1.44 µm in the case of the present embodiment) is taken as cross-section area $A_1$. In the same way, the selected identification symbol is sequentially changed, whereby the average flow velocity $u_2, u_3, \ldots, u_n$, and cross-section area $A_2, A_3, \ldots, A_n$, can be derived for the n virtual curved surface solids within the cross-section. The in-plane uniformity index evaluation module 25d then derives the in-plane uniformity index $\gamma_7$ for multiple cross-sections, e.g., 250 (=300 µm/1.2 µm) cross-sections with the distance x changed 1.2 µm at a time for example. Determination is made that the pressure drop property of the porous body is acceptable when the average value of the in-plane uniformity index $\gamma_x$ is 0.6 or greater, and unacceptable when smaller than 0.6. Note that at the time of deriving the in-plane uniformity index $\gamma_x$, multiple in-plane uniformity indices $\gamma_x$ are preferably derived by changing the distance x by a value the same as the X direction length of the pixels (1.2 µm with the present embodiment), i.e., shifting the cross-section which is the object of derivation one pixel at a time. However, an arrangement may be made not restricted to this, where the distance x is changed and multiple in-plane uniformity indices $\gamma_x$ are derived. Also, an arrangement may be made where just one in-plane uniformity index $\gamma_x$ is derived and acceptability determination is made by whether or not that value is 0.6 or greater.

[Math. 1]

$$\gamma_x = 1 - \frac{1}{2}\sum_{i=1}^{n}\frac{|u_i - u_{mean}| \cdot A_i}{u_{mean} \cdot A} \qquad \text{Expression (1)}$$

where:
n: number [count] of virtual curved surface solids within cross-section:
x: distance [m] between cross-section and inflow face:
$u_i$: average flow velocity (i=1, 2, ..., n) [m/s] for each of the n virtual curved surface solids at cross-section;
$u_{mean}$: average value (=($u_1+u_2+\ldots+u_n$)/n) [m/s] of average flow velocity $u_i$ at cross-section;
$A_i$: cross-sectional area (i=1, 2, ..., n) [m$^2$] for each virtual curved surface solid within cross-section; and
A: total cross-sectional area (=$A_1+A_2+\ldots+A_n$) [m$^2$] of virtual curved surface solids at cross-section.

Next, the spatial uniformity index evaluation module 25e performs spatial uniformity index evaluation processing where a spatial uniformity index $\gamma$ is derived, and acceptability determination is made on the derived value to evaluate the porous body (step S130). The spatial uniformity index $\gamma$ is derived by the following Expression (2) using multiple in-plane uniformity indices $\gamma_x$ derived in the in-plane uniformity index evaluation processing. Determination is made that the collection performance of the porous body is acceptable when the derived spatial uniformity index $\gamma$ is 0.6 or greater, and unacceptable when smaller than 0.6. Also note that acceptability may be determined based on whether or not 0.5 or greater.

[Math. 2]

$$\gamma = \overline{\gamma_x} \cdot (1 - \delta_\gamma) \qquad \text{Expression (2)}$$

where:
$\overline{\gamma_x}$: average value of $\gamma_x$; and
$\delta_\gamma$: standard deviation of $\gamma_x$.

Next, the pressure drop evaluation module 25f performs pressure drop evaluation processing where the pressure drop P per unit thickness is derived, and acceptability determination is made on the derived value to evaluate the porous body (step S140). The pressure drop P is derived by the following Expression (3) using multiple in-plane uniformity indices $\gamma_x$ derived in the in-plane uniformity index evaluation processing. This Expression (3) is one where a known Ergun's Equation representing pressure drop properties at the time of a fluid passing through a porous body, has been revised using the in-plane uniformity index $\gamma_x$. Note that the representative hydraulic diameter $Dh_x$ of the space (pores) at the cross-section at distance x is obtained as follows with the present embodiment. First, a total area $A_x$ is derived, with the total area of space portions at the cross-section at distance x as $A_x$. This is derived as the product of the number of pixels of the space pixels at the cross-section at distance x (including curved surface solid pixels), and the cross-sectional area of each pixel (1.44 µm² with the present embodiment). Next, the total wetted perimeter $L_x$ is derived with the total of wetted perimeters at the cross-section at distance x as $L_x$. This is derived as the total of the length of boundary lines between space pixels (including curved surface solid pixels) and matter pixels. The representative hydraulic diameter $Dh_x$ is then derived from representative hydraulic diameter $Dh_x$=4×total area $A_x$/total wetted perimeter $L_x$. Note that it is sufficient for the representative hydraulic diameter $Dh_x$ to be a value representing the diameter of the space (pores) at the cross-section at distance x, and may be derived by another method. For example, a cross-sectional equivalent diameter $Re_i$ of a virtual curved surface solid at the cross-section at the distance x may be obtained for each virtual curved surface solid within the cross-section, and the average value of this cross-sectional equivalent diameter $Re_i$ may be derived as the representative hydraulic diameter $Dh_x$. The cross-sectional equivalent diameter $Re_i$ of a virtual curved surface solid may be obtained by $Re_i$=4×cross-sectional area $A_i$/perimeter $L_i$, for example. In this Expression, the cross-sectional area Ai may be obtained by the method described above. The perimeter $L_i$ may be obtained as the length of the cross-sectional outline of the virtual curved surface solid projected on the cross-section at the distance x, based on information included in the virtual curved surface solid table 83, for example. Also, a flow velocity average value $U_x$ for every space pixel at the cross-section at the distance x described below may be derived by, for example, finding the flow velocity vectors correlated with each space pixel in the fluid analysis processing for the space pixels (including curved surface solid pixels) at the cross-section at the distance x, deriving the flow velocity component in a direction perpendicular to the cross-section of each space pixel, and deriving as the average value thereof. Note that a constant k can be obtained beforehand by experiment, for example, so that the correlation between the pressure drop P and the actual pressure drop of the porous body is higher. With the present embodiment, the constant k is set to the value "−2". Also, the acceptability determination based on pressure drop P is performed as follows, for example. First, the pressure drop P is derived for each of the multiple in-plane uniformity indices $\gamma_x$, and the average value of the multiple pressure drops P is derived. In the event that the average value of the pressure drops P is at or below a predetermined threshold (e.g., allowable upper limit value of pressure drop), determination is made that the pressure drop of the porous body is acceptable, and determined to be unacceptable if the predetermined threshold is exceeded. At the time of deriving the multiple pressure drops P with the present embodiment, the distance x is changed by a value the same as the X direction length of the pixels (1.2 µm with the present embodiment), i.e., shifting the cross-section which is the object of derivation one pixel at a time, and pressure drops P of a number corresponding to as many in-plane uniformity indices $\gamma_x$ as there are pixels in the X direction are derived. However, the method for deriving the average value of pressure drops P is not restricted to this, and any method will suffice as long as pressure drops P corresponding to multiple in-plane uniformity indices $\gamma_x$ are derived while changing the distance x, and the average thereof is derived.

[Math. 3]

$$P = \frac{\Delta P_x}{\Delta x} = \left( \frac{200}{3} \frac{1}{D_{hx}^2 \cdot \varepsilon_k} \mu U_x + \frac{7}{6} \frac{1}{D_{hx} \cdot \varepsilon_x^2} \rho U_x^2 \right) \cdot \gamma_x^k \qquad \text{Expression (3)}$$

where:

$\Delta x$: cross-sectional thickness [m] at cross-section at distance x;

$\Delta P_x$: pressure drop [Pa] at cross-section at distance x;

$Dh_x$: representative hydraulic diameter [m] of space (pores) at cross-section at distance x;

$\varepsilon_x$: voidage (=number of space pixels/(number of space pixels+number of matter pixels)) at cross-section at distance x;

µ: viscosity [Pa·s] of fluid;

$U_x$: flow velocity average value [m/s] at each space pixel at cross-section at distance x;

ρ: density of fluid [kg/m³]; and k: constant.

Next, the flow-through velocity evaluation module 25g performs flow-through velocity evaluation processing where the flow-through velocity T at each virtual curved surface solid is derived, the virtual curved surface solids are classified based on the derived values, and the porous body is evaluated based on the classification results (step S150). The flow-through velocity T at each virtual curved surface solid is derived as follows, for example. First, a through-flow volume Q per unit time of the fluid is derived for each virtual curved surface solid. The flow-through velocity T of each virtual curved surface solid is then derived by T=Q/(πd²/4), based on the derived through-flow volume Q and an equivalent diameter d of the virtual curved surface solid (=6× volume V of virtual curved surface solid/surface area S of virtual curved surface solid). The through-flow volume Q, volume V, and surface area S of each virtual sphere is derived as follows, for example. First, one virtual curved surface solid is selected, and the curved surface solid pixels corresponding to the identification symbols of the selected virtual curved surface solid are found from the porous body table 81 in the RAM 24. The number of pixels of the curved surface solid pixels configuring the selected virtual curved surface solid is derived, and the product of the number of pixels and the volume of one curved surface solid pixel (1.728 µm³ with the present embodiment) is taken as the volume V. Also, the surface area S of the selected virtual curved surface solid is derived based on information (center coordinate and diameter of parent virtual sphere and child virtual spheres) included in the virtual curved surface solid table 83. Next, of the curved surface solid pixels configuring the selected virtual curved surface solid, the curved surface solid pixel configuring the surface of the virtual curved surface solid are identified based on the information included in the virtual curved surface solid table 83. The flow vectors correlated with the curved surface solid pixels configuring the surface are found using the porous body table 81 in the RAM 24, the curved surface solid pixels of which the flow velocity vector heads toward the inside of the virtual curved surface solid are identified, the magnitude of the flow velocity vectors of the identified curved surface solid pixels is obtained for each curved surface solid pixel, and derived as through-flow volume Q per unit time=(sum of magnitude of flow velocity vectors)×(number of identified curved surface solid pixels)×(area of one face of a curved surface solid pixel (=1.44 µm²)). Thus, the flow-through velocity T of the selected curved surface solid pixel can be derived. In the same way, the flow-through velocity T is derived for each of the multiple virtual curved surface solids.

Classification of each of virtual curved surface solids in the flow-through velocity evaluation processing is performed as follows. First, one virtual curved surface solid is selected, and a flow velocity ratio $T_f(=T/T_{in})$ is derived from the flow-through velocity T of the selected virtual curved surface solid and the average flow velocity $T_{in}$ in fluid analysis. In the event that $T_f<2$, that virtual curved surface solid is classified as being a low-flow-velocity curved surface solid, in the event that $2 \leq T_f < 8$, as being a mid-flow-velocity curved surface solid, and in the event that $8 \leq T_f$, as being a high-flow-velocity curved surface solid. Each of the virtual curved surface solids are classified in the same way. In the event that the percentage of the total value of volume V of the low-flow-velocity curved surface solid is 20% or less as to the total value of volume V of the multiple virtual curved surface solids, and also the percentage of the total value of volume V of the high-flow-velocity curved surface solid is 10% or less, determination is made that the performance of the porous body is acceptable. On the other hand, in the event that the percentage of the total value of volume V of the low-flow-velocity curved surface solid is greater than 20%, or that the percentage of the total value of volume V of the high-flow-velocity curved surface solid is greater than 10%, determination is made that the performance of this porous body is unacceptable.

Next, the equivalent diameter evaluation module 25h performs equivalent diameter evaluation processing in which the equivalent diameter d of each virtual sphere is derived, the virtual curved surface solids are classified based on the equivalent diameter d, and the porous body is evaluated based on the classification results (step S160). Classification of the virtual curved surface solids based on the equivalent diameter d is performed by taking a virtual curved surface solid where d<10 μm as being a small-diameter curved surface solid, a virtual curved surface solid where 10 μm≤d≤25 μm as being a mid-diameter curved surface solid, and a virtual curved surface solid where 25 μm<d as being a large-diameter curved surface solid. In the event that the percentage of the total value of volume V of mid-diameter curved surface solids as to the total value of volume V of the multiple virtual curved surface solids is 70% or more, determination is made that the performance of the porous body is acceptable, and in the case of less than 70%, determination is made that the performance of the porous body is unacceptable. Note that the equivalent diameter d and the volume V may be derived in the same way as with the flow-through velocity evaluation processing described above, or values derived in the flow-through velocity evaluation processing may be used without change.

Upon performing each evaluation processing of steps S120 through S160, the analysis result output module 25i performs analysis result output processing in which the information and the like stored in the RAM 24 in the above processing is output as analysis result data and stored in the HDD 25 (step S170), and the present routine ends. The analysis result data includes, for example, the porous body data 80 including the porous body table 81, inflow/outflow table 82, and virtual curved surface solid table 83, stored in the RAM 24, the values and the result of acceptability determination of the in-plane uniformity index $\gamma_x$ in the in-plane uniformity index evaluation processing, the values and the result of acceptability determination of the spatial uniformity index $\gamma$ in the spatial uniformity index evaluation processing, the values and the result of acceptability determination of the pressure drop P in the pressure drop evaluation processing, the flow-through velocity T in the flow-through velocity evaluation processing, flow velocity ratio $T_f$ value, percentage of the total value of volume V of low-flow-velocity curved surface solids, and percentage of the total value of volume V of high-flow-velocity curved surface solids and the result of acceptability determination, the values of equivalent diameter d in the equivalent diameter evaluation processing, and percentage of the total value of volume V of mid-diameter curved surface solids and the result of acceptability determination, and so forth. Values used for the fluid analysis processing, such as average flow velocity $T_{in}$, fluid viscosity μ, fluid density ρ, and so forth may also be included.

Note the correlation between the components of the present embodiment and the microstructure analysis device according to the present invention will be disclosed. The RAM 24 and HDD 25 according to the present embodiment correspond to storage units of the present invention, the virtual curved surface solid placement module 25b corresponds to virtual curved surface solid placement unit, and the in-plane uniformity index evaluation module 25d, spatial uniformity index evaluation module 25e, pressure drop evaluation module 25f, flow-through velocity evaluation module 25g, and equivalent diameter evaluation module 25h correspond to microstructure analysis unit. Note that with the present embodiment, an example of the microstructure analysis method according to the present invention is also disclosed by describing the operations of the user PC 20.

According to the present embodiment described in detail above, porous body data 80 in which position information and type information is correlated is referenced to take a curved surface solid made up of a parent virtual sphere and child virtual spheres as a virtual curved surface solid, and multiple virtual curved surface solids are placed so as to fill in space pixels with curved surface solid pixels occupied by virtual curved surface solids, whereby the space inside a porous body can be simulated more precisely as a group of multiple virtual curved surface solids. The microstructures of porous bodies can then be analyzed more precisely, by being based on information relating to these virtual curved surface solids. Also, the virtual curved surface solids are placed so that the virtual curved surface solids do not overlap each other or curved surface solid pixels and matter pixels overlap each other, so the processing time necessary to place the virtual curved surface solids can be reduced as compared to a case where overlapping is permitted. Further, the diameter Ra is first set to the maximum value Rmax and whether or not a parent virtual sphere can be placed is determined while sequentially decrementing Ra, so the space pixels can be filled with as large a virtual curved surface solid as possible.

Also, the in-plane uniformity index $\gamma_x$ is derived, and acceptability determination is performed based thereupon. Now, the more uniform the flow velocity of a fluid at a cross-section is, the greater (closer to value 1) the in-plane uniformity index $\gamma_x$ is, and the greater the irregularity in the flow velocity of a fluid at a cross-section is, the smaller the value is. In a case of using the porous body for a filter, the greater the value of the in-plane uniformity index $\gamma_x$ is, the better the pressure drop property tends to be. Accordingly, deriving this in-plane uniformity index $\gamma_x$ and performing evaluation based thereupon enables the pressure drop property of the porous body to be evaluated more precisely, as microstructure analysis.

Further, the spatial uniformity index $\gamma$ is derived and acceptability determination is performed based thereupon. Now, the smaller the irregularity in the in-plane uniformity index $\gamma_x$ derived regarding multiple cross-sections is, the greater the spatial uniformity index $\gamma$ is, and the greater the irregularities, the smaller the value is. The collecting performance in the case of using the porous body for a filter tends to be better the greater this spatial uniformity index $\gamma$ is. Accordingly, by deriving this spatial uniformity index $\gamma$ and performing evaluation based thereupon enables the collecting performance of the porous body to be evaluated more precisely, as microstructure analysis.

Moreover, the pressure drop P per unit thickness is derived, and acceptability determination is performed based thereupon. Now, the pressure drop P has greater correlation with the pressure drop of an actual porous body as compared with the pressure drop derived by Ergun's Equation. Accordingly, pressure drop property of a porous body, for example, can be evaluated more precisely by deriving this pressure drop P per unit volume and performing evaluation based thereupon, as microstructure analysis.

Also, the flow-through velocity T is derived, the virtual curved surface solids are classified based thereupon, and acceptability determination is performed based on the classification results. Now, there are cases where pores of a porous body simulated with virtual curved surface solids of which the flow-through velocity T is small may not contribute much to transmittance of the fluid, leading increased pressure drop, and deterioration in thermal conductivity and thermal capacity of the material. Also, there are cases where pores of a porous body simulated with virtual curved surface solids of which the flow-through velocity T is great exhibit great flow resistance when the fluid passes through, or the fluid may pass through in a short time and the pores do not contribute much to collecting performance. Accordingly, classifying a part of the virtual curved surface solids as low-flow-velocity curved surface solids with small flow-through velocity T and high-flow-velocity curved surface solid with great flow-through velocity T in this way, and performing evaluation based thereupon, enables the microstructure of the porous body to be analyzed precisely.

Also, the equivalent diameter d is derived, the virtual curved surface solids are classified based thereupon, and acceptability determination is performed based on the classification results. Now, there are cases where pores of the porous body simulated with virtual curved surface solids of which the equivalent diameter d is small, the flow velocity of the fluid passing through become small and leading to increased pressure drop, or the catalyst applied to the walls of the pores to use the porous body as a filter may not be appropriately applied, or the like. Also, there are cases where pores of the porous body simulated with virtual curved surface solids of which the equivalent diameter d is great, the flow velocity of the fluid passing through become great, and not contributing to collecting performance very much when using the porous body as a filter. Accordingly, classifying a part of the virtual curved surface solids as virtual curved surface solids with small equivalent diameter d and virtual curved surface solids with great equivalent diameter d in this way, and performing evaluation based thereupon, enables the microstructure of the porous body to be analyzed precisely.

Note that the present invention is not restricted to the above-described embodiment by any means, and may be realized in various forms without departing from the technical scope of the present invention, as a matter of course.

For example, while the above-described embodiment has one parent virtual sphere placed in one virtual curved surface solid in the virtual curved surface solid placement processing, this may be multiple. In the event that there are multiple parent virtual spheres, the virtual curved surface solid may be made up of multiple parent virtual spheres and one or more child virtual spheres of which pixels occupied thereby partially overlap with at least one of the multiple parent virtual spheres. Also, in the event that multiple child virtual spheres are to be placed at the time of placing one virtual curved surface solid, mutual overlapping of multiple child virtual spheres has been permitted, but this may not be permitted.

With the above-described embodiment, the virtual curved surface solids have been placed in the virtual curved surface solid placement processing such that the center of child virtual spheres overlap the parent virtual sphere, but unrestricted to this, pixels occupied by a child virtual sphere and pixels occupied by a parent virtual sphere may partially overlap.

With the above-described embodiment, the virtual curved surface solids have been placed in the virtual curved surface solid placement processing such that a virtual curved surface solid does not overlap pixels occupied by another virtual curved surface solid, but partial overlapping may be permitted. Also, the virtual curved surface solids have been placed such that curved surface solid pixels and matter pixels do not overlap, but partial overlapping may be permitted.

With the above-described embodiment, fluid analysis has been performed by the lattice Boltzmann method, but another fluid analysis method may be used.

With the above-described embodiment, determination has been made in the flow-through velocity evaluation processing that the performance of the porous body is acceptable in the event that the percentage of the total value of volume V of the low-flow-velocity curved surface solids is 20% or less as to the total value of volume V of the virtual curved surface solids, and also the percentage of the total value of volume V of the high-flow-velocity curved surface solid is 10% or less, however, the performance of the porous body may be determined to be acceptable when the volume ratio of the low-flow-velocity curved surface solids in the virtual curved surface solids is at or below a predetermined threshold, and the volume ratio of the high-flow-velocity curved surface solids in the virtual curved surface solids is at or below a predetermined threshold. The threshold for the low-flow-velocity curved surface solids and the threshold for the high-flow-velocity curved surface solids are not restricted to the above-described 20% and 10%, and may be values obtained by experiments, for example. Also, the performance of the porous body may be determined to be acceptable when the volume ratio of the low-flow-velocity curved surface solids in the virtual curved surface solids is at or below a predetermined threshold, or the performance of the porous body may be determined to be acceptable when the volume ratio of the high-flow-velocity curved surface solids in the virtual curved surface solids is at or below a predetermined threshold.

Also, with the above-described embodiment, classification has been performed such that virtual curved surface solids where $T_f<2$ are classified as the low-flow-velocity curved surface solids, virtual curved surface solids where $2 \leq T_f < 8$ as the mid-flow-velocity curved surface solids, and virtual curved surface solids where $8 \leq T_f$ as the high-flow-velocity curved surface solids, but classification may be performed with other thresholds. And moreover classification of virtual curved surface solids is not restricted to that performed by the flow velocity ratio $T_f$, and classification may be performed by comparing the flow-through velocity T and threshold values.

With the above-described embodiment, in the equivalent diameter evaluation processing, a virtual curved surface solid where $10 \ \mu m \leq d \leq 25 \ \mu m$ has been taken as a mid-diameter curved surface solid, and in the event that the percentage of the total value of volume V of mid-diameter curved surface solids as to the total value of volume V of the virtual curved surface solids is 70% or more, determination has been made that the performance of the porous body is acceptable, but this is not restricted to 70%, and another threshold obtained by experiment may be used to determine acceptability. For example, determination may be made to be acceptable in the case of 60% or more. Also, classification and evaluation of curved surface solids may be made by another method. For example, virtual curved surface solids where $d<10 \ \mu m$ are taken as being small-diameter curved surface solids, and in the event that the percentage of the total value of volume V of the small-diameter curved surface solids as to the total value of volume V of the virtual curved surface solids is 25% or less, determination may be made that the porous body is acceptable. Also, virtual curved surface solids where $30 \ \mu m \leq d$ may be taken as large-diameter curved surface solids, and in the event that the percentage of the total value of volume V of the large-diameter curved surface solids as to the total value of volume V of the virtual curved surface solids is 10% or less, determination may be made that the porous body is acceptable, or determination of being acceptable may be made with 5% or less. Further, virtual curved surface solids where 40 µm≤d may be taken as large-diameter curved surface solids, and determination may be made that the porous body is acceptable when no large-diameter curved surface solids exist.

With the above-described embodiment, the in-plane uniformity index $\gamma_x$, spatial uniformity index $\gamma$, and pressure drop P are derived and determination of acceptability has been performed in the analysis processing routine, but an arrangement may be made where the values are derived but determination of acceptability is not performed. Also, while deriving of the flow-through velocity T and equivalent diameter d, classification, and determination of acceptability have been performed in the analysis processing routine, but an arrangement may be made where determination of acceptability is not performed, or an arrangement may be made where classification and determination of acceptability are not performed.

With the above-described embodiment, each process of steps S120 through S140 have been performed, but one or both of steps S130 and S140 may be omitted, or all of steps S120 through S140 may be omitted. In the same way, one or more of each process of steps S150 through S170 may be omitted. Also, in the case of omitting all processes of steps SS120 through S160, the process of step S110 may be omitted.

With the above-described embodiment, virtual curved surface solids where, of an n number of average flow velocities $u_i$, the average flow velocity $u_i$ is of a value 0, may be excluded from the n virtual curved surface solids, deeming that this is a space enclosed by the component material of the porous partition 44 and does not affect flow of the fluid. For example, if there are five virtual curved surface solids within a cross-section, and the average flow velocity $u_i$ of one virtual curved surface solid is of the value 0, this virtual curved surface solid may be ignored (deemed to be matter pixels), and the subsequent processing continued deeming that there are four virtual curved surface solids in the cross-section and the at the number n=4. Other processing using the results of this fluid analysis may be the same.

With the above-described embodiment, in deriving the equivalent diameter d (=6×volume V of virtual curved surface solid/surface area S of virtual curved surface solid), the product of the number of pixels of the curved surface solid pixels configuring the virtual curved surface solid and the volume of one curved surface solid pixel (1.728 µm³ with the present embodiment) is taken as the volume V, but is not restricted to this. For example, the volume V of the virtual curved surface solid may be derived based on information (center coordinate and diameter of parent virtual sphere and child virtual spheres) included in the virtual curved surface solid table 83. That is to say, instead of volume in a case of considering the virtual curved surface solid to be a group of space pixels (the edge portion of the virtual curved surface solid is represented as the edge portion of space pixels, i.e., by straight lines and planes), the volume V may be taken as the volume in a case of considering the virtual curved surface solid to be a group of a parent virtual sphere and child virtual spheres represented by center coordinates and diameter (the edge portion of the virtual curved surface solid is represented by curves and curved surfaces).

With the above-described embodiment, the cross-sectional area $A_i$ ($A_1, A_2, A_3, \ldots, A_n$) has been derived from the product of the number of pixels and the area of the curved surface solid pixels following the cross-section (1.44 µm² in the case of the present embodiment), but is not restricted to this. For example, the cross-sectional area $A_i$ of a virtual curved surface solid may be derived based on the center coordinates and diameter of the parent virtual sphere and child virtual sphere included in the virtual curved surface solid table 83, and the position of the cross-section (distance x between cross-section and inflow face 61). That is to say, instead of area in a case of considering the virtual curved surface solid to be a group of space pixels (the edge portion of the cross-section is represented as the edge portion of space pixels, i.e., by straight lines), the cross-sectional area $A_i$ may be taken as the area in a case of considering the virtual curved surface solid to be a group of a parent virtual sphere and child virtual spheres represented by center coordinates and diameter (the edge portion of the cross-section is represented by curves).

With the above-described embodiment, the flow-through velocity T has been derived by $T=Q/(\pi d^2/4)$, but is not restricted to this. For example, flow-through velocity components Tx, Ty, and Tz may be derived for the X, Y, and Z directions of the virtual curved surface solid, with the flow-through velocity T being derived as flow-through velocity $T=\sqrt{(Tx^2+Ty^2+Tz^2)}$. The flow-through velocity component Tx in this case is derived as follows. First, regarding the virtual curved surface solid which the flow-through velocity T is to be derived, a cross-section which passes through the center of the parent virtual sphere of a virtual curved surface solid, and also is perpendicular to the X direction, is identified, and curved surface solid pixels configuring that cross-section are identified. Next, the X direction components of the flow velocity vectors correlated with each of the identified curved surface solid pixels (magnitude of flow velocity vectors in the X direction) are found using the porous body table 81, and the average value thereof is taken as the flow-through velocity component Tx. In the same way, curved surface solid pixels configuring a cross-section which passes through the center of the parent virtual sphere of the virtual curved surface solid, and also is perpendicular to the Y direction, are identified. The average value of the Y direction components of the flow velocity vectors of the curved surface solid pixels is taken as the flow-through velocity component Ty. Also, curved surface solid pixels configuring a cross-section which passes through the center of the parent virtual sphere of the virtual curved surface solid, and also is perpendicular to the Z direction, are identified. The average value of the Z direction components of the flow velocity vectors of the curved surface solid pixels is taken as the flow-through velocity component Tz.

With the above-described embodiment, in the virtual curved surface solid placement processing, the virtual curved surface solids have been placed such that a virtual curved surface solid does not overlap pixels occupied by another virtual curved surface solid, but overlapping of occupied pixels (the virtual curved surface solids overlapping each other) may be permitted. Thus, virtual curved surface solids with as large a volume as possible can be placed as compared with a case where virtual curved surface solids are placed so as to not overlap. Also, the space within the porous body can be simulated more precisely with virtual curved surface solids by placing virtual curved surface solid having as large a volume as possible. Also, avoiding placing virtual curved surface solids with small volume in a case of placing the virtual curved surface solids such that the virtual curved surface solids do not overlap with occupied pixels of another virtual curved surface solid, there are cases where space pixels where no virtual curved surface solid is placed increases. That is to say, there are cases where, of the space within the porous body, space which cannot be simulated with virtual curved surface solids increases. However, permitting the virtual curved surface solids to overlap each other enables reduction in such space which cannot be simulated with virtual curved surface solids. Permitting overlapping of virtual curved surface solids can be realized by permitting placement of a parent virtual sphere in step S230 in the virtual curved surface solid placement processing in FIG. 7 described above, even in cases where placing a parent virtual sphere having a diameter Ra overlaps with an already-placed virtual curved surface solid. For example, determination may be made in step S230 that the parent virtual sphere of the diameter Ra can be placed at that position regardless of whether the parent virtual sphere overlaps an already-placed virtual curved surface solid, as long as the parent virtual sphere of the diameter Ra does not overlap matter pixels. In the same way, this can be realized by permitting placement of a child virtual sphere in step S270 even in cases where placing a child virtual sphere having a diameter Rb overlaps with an already-placed virtual curved surface solid. For example, determination may be made in step S270 that the child virtual sphere of the diameter Rb can be placed at that position regardless of whether the child virtual sphere overlaps an already-placed virtual curved surface solid, as long as the child virtual sphere of the diameter Rb does not overlap matter pixels. Note that in the case of permitting overlapping of virtual curved surface solids, the center of a parent virtual sphere or child virtual sphere may overlap a virtual curved surface solid already placed. Also, in the case of permitting overlapping of virtual curved surface solids, when deriving numerical values combining information relating to the multiple virtual curved surface solids such as the sum of volume or sum of cross-sectional area of the multiple virtual curved surface solids, calculation is preferably performed assuming that the portions where multiple virtual curved surface solids overlap belong to only one of the virtual curved surface solids. On the other hand, when calculating values regarding each of the individual virtual curved surface solids, such as when deriving the cross-sectional area or surface area of a virtual curved surface solid, or deriving the equivalent diameter d, or the like, calculation is preferably performed assuming that the portions where the multiple virtual curved surface solids overlap belong to each virtual curved surface solid. Note that in the event of making a portion where multiple virtual curved surface solids overlap to belong to one virtual curved surface solid, this may be made to belong to the virtual curved surface solid of which the diameter of the parent virtual sphere is the greatest, for example, or to belong to the virtual curved surface solid of which the equivalent diameter d is the greatest.

With the above-described embodiment, the center of the parent virtual sphere or child virtual sphere has been the center of a pixel, but is not restricted to this. It is sufficient for the center of the parent virtual sphere or child virtual sphere to be within a pixel. For example, the center of the parent virtual sphere or child virtual sphere may be at the edge of the pixel closest to the origin of the XYZ coordinates.

With the above-described embodiment, the pressure drop evaluation module 25f has derived the pressure drop P per unit thickness, but in addition to or instead of this, may derive the pressure drop index $P_e$ of the porous body. Hereinafter, the pressure drop index $P_e$ will be described. The pressure drop index $P_e$ is obtained by $P_e$=(wetted area $A_W$ of space within porous body/pore volume $V_p$ of space within porous body)×(1/porosity ϵ of porous body)×(average value $L_{fmean}$/distance L between inflow face and outflow face). The wetted area $A_W$ [μm²] of space within the porous body is derived as the product of the number of boundaries between space pixels (including curved surface solid pixels) and matter pixels in the porous body data 80, and the area at one boundary face (1.44 μm² in the embodiment described above). The pore volume $V_p$ [μm] of space within the porous body is derived as the product of the number of space pixels (including curved surface solid pixels) in the porous body data 80, and the volume of one pixel (1.728 μm³ in the embodiment described above). The porosity ϵ is derived by deriving the number of space pixels (including curved surface solid pixels) and matter pixels in the porous body data 80, and derived by porosity ϵ=number of space pixels/(number of space pixels+number of matter pixels). The distance L [||m] between inflow face and outflow face is derived based on the inflow/outflow table 82. For example, with the above-described embodiment, the inflow face 61 is a plane where X=1, and the outflow face 62 is a plane where X=251, so the distance L=(251−1)×1.2 μm=300 μm. The average value $L_{fmean}$ is obtained as follows. Multiple path lengths $L_f$ are derived from one of a predetermined inflow face and a predetermined outflow face of the porous body to the other face, following adjacent or overlapping virtual curved surface solids. The average the microstructure of the porous body may be analyzed by deriving multiple path lengths $L_f$ from one of a predetermined inflow face and a predetermined outflow face of the porous body to the other face following adjacent or overlapping virtual curved surface solids, deriving an average value of the multiple path lengths $L_f$ is derived as the average value $L_{fmean}$.

Figure 11:
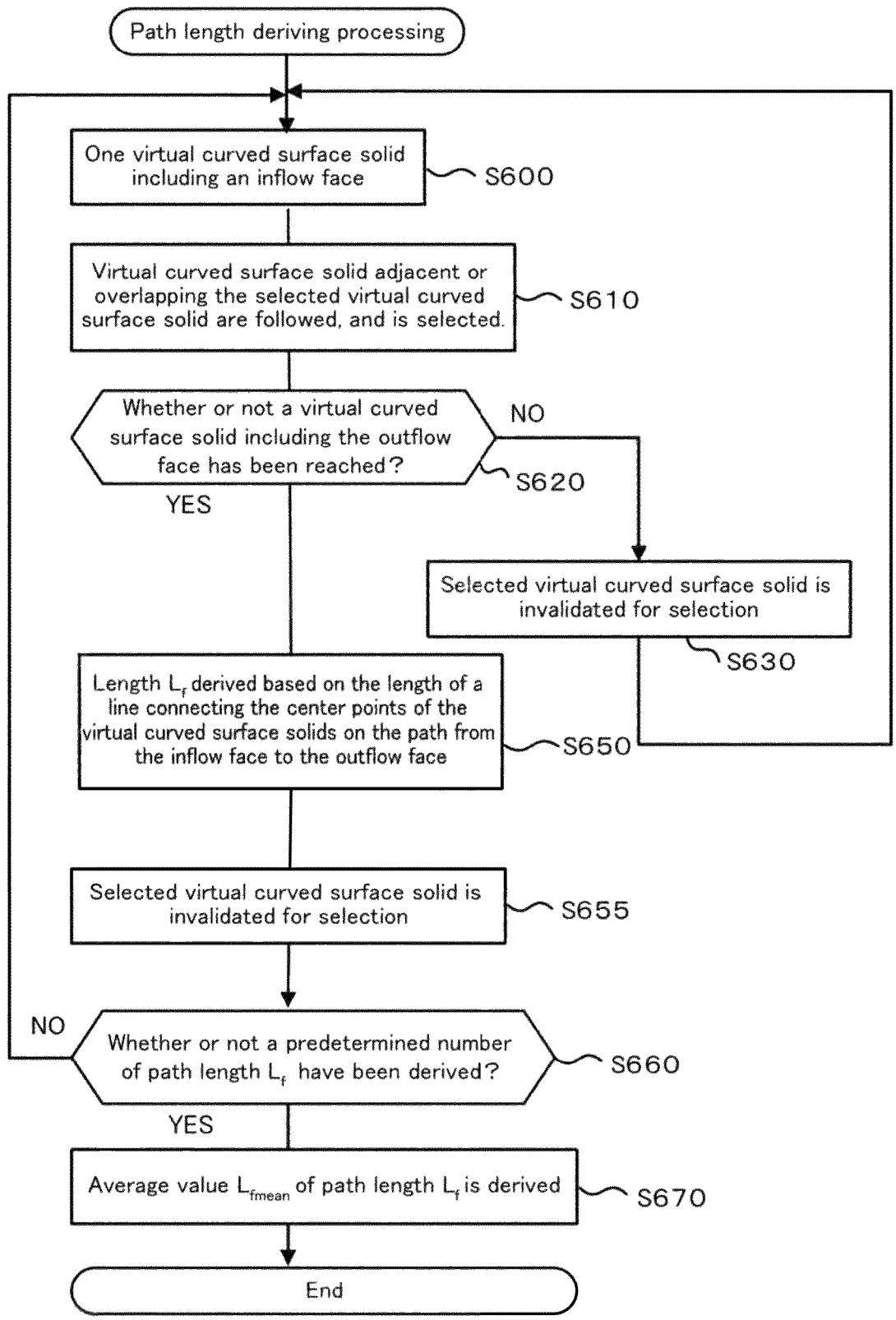
FIG. 11 is a flowchart illustrating an example of path length deriving processing.

Now, a method for deriving the path length $L_f$ and average value $L_{fmean}$. FIG. 11 is a flowchart illustrating an example of path length deriving processing. As illustrated in FIG. 11, with the path length deriving processing, first, one virtual curved surface solid including an inflow face 61 is selected (step S600). Whether or not a virtual curved surface solid includes an inflow face 61 can be determined from the center coordinates and diameter of the parent virtual sphere and the center coordinates and diameter of the child virtual spheres of each virtual curved surface solid stored in the virtual curved surface solid table 83 created in the virtual curved surface solid placement processing, and the mathematical expression (X=1) expressing the inflow face 61 stored as the inflow/outflow table 82. Also, in step S600, virtual curved surface solids which are not selectable in the later-described step S630 or S655 is not selected. Next, virtual curved surface solids adjacent or overlapping the selected virtual curved surface solid are followed, and all are selected (step S610). Deriving of the virtual curved surface solids adjacent or overlapping the selected virtual curved surface solid is performed as follows, for example. First, of the curved surface solid pixels occupied by the selected virtual curved surface solid, one curved surface solid pixel situated on the surface of the virtual curved surface solid is selected. Whether or not there is another virtual curved surface solid occupying a curved surface solid pixel adjacent to that curved surface solid pixel is found, and in the event that there is, that virtual curved surface solid is derived as an adjacent virtual curved surface solid. In the same way, in the event that there are other virtual curved surface solids occupying curved surface solid pixels situated on the surface of the selected virtual curved surface solid, these virtual curved surface solids are derived as being overlapping virtual curved surface solids. Note that this is not restricted to the method using curved surface solid pixels in this way, and that virtual curved surface solids adjacent to or overlapping the selected virtual curved surface solid may be derived based on the center coordinates and diameter of the parent virtual sphere and the center coordinates and diameter of the child virtual spheres of each virtual curved surface solid stored in the virtual curved surface solid table 83, for example. Also, in the event of not permitting overlapping virtual curved surface solids in the virtual curved surface solid placement processing, it is sufficient to sequentially follow virtual curved surface solids adjacent to the selected virtual curved surface solid. Upon having performed the processing of step S610, determination is made regarding whether or not a virtual curved surface solid including the outflow face 62 has been reached (step S620). This processing is performed by determining whether or not there is a virtual curved surface solid including the outflow face 62 in the selected virtual curved surface solids. Note that the determination method of whether or not a virtual curved surface solid includes the outflow face 62 is the same as with the above determination of whether or not the inflow face 61 is included. In the event that a virtual curved surface solid including the outflow face 62 is not reached, all selected virtual curved surface solids are invalidated for selection (step S630), and processing of step S600 and thereafter is performed. On the other hand, in the event that a virtual curved surface solid including the outflow face 62 is reached in step S620, the path length $L_f$ is derived based on the length of a line connecting the center points of the virtual curved surface solids on the path from the inflow face 61 to the outflow face 62 (S650). Note that the center point of a virtual curved surface solid means the center of the parent virtual sphere. Also, the path length $L_f$ includes the distance from the inflow face 61 to the center of the virtual curved surface solid including the inflow face 61, and the distance from the outflow face 62 to the center of the virtual curved surface solid including the outflow face 62. Upon having derived the path length $L_f$ in step S650, all virtual curved surface solids being selected are invalidated for selection (step S655). Determination is made regarding whether or not a predetermined number of path lengths $L_f$ have been derived (step S660), and in the event that the number of derived path lengths $L_f$ is less than a predetermined number, the processing of step S600 and thereafter is performed. Also, in the event that the number of path lengths $L_f$ derived in step S660 has reached the predetermined number, the average value of the multiple derived path lengths $L_f$ is derived as the average value $L_{fmean}$ (step S670), and the path length deriving processing ends. Note that the predetermined number (number of path lengths $L_f$ to be derived) in step S660 is preferably 600 or more. However, the number of path lengths $L_f$ to be derived is not restricted to this, and may be set as appropriate in accordance with calculation load and precision. Also, while the path length deriving processing in FIG. 11 has been described as processing where virtual curved surface solids adjacent or overlapping each other are followed from the inflow face of the porous body toward the outflow face to derive the path length $L_f$, but virtual curved surface solids may be followed from the outflow face of the porous body toward the inflow face to derive the path length $L_f$.

Figure 12:
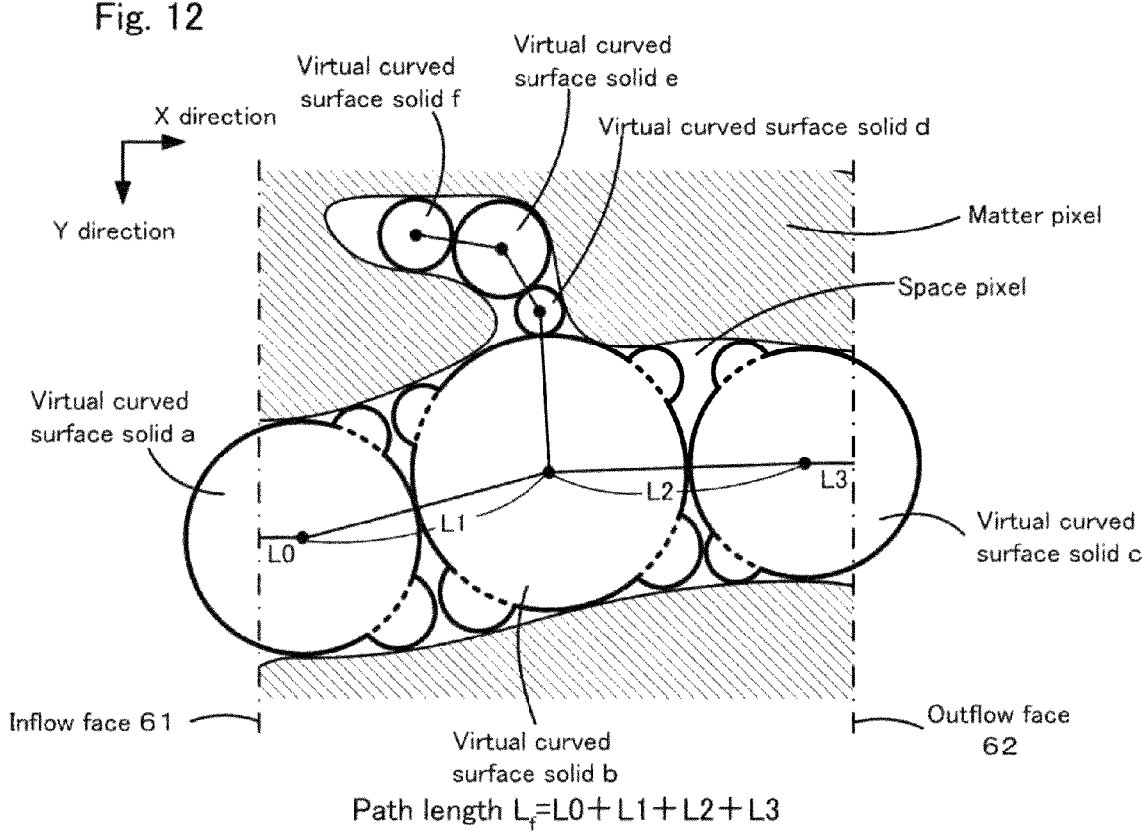
FIG. 12 is an explanatory diagram illustrating the way in which a path length $L_f$ is derived.

FIG. 12 is an explanatory diagram illustrating the way in which a path length $L_f$ is derived. In the event that virtual curved surface solids a through f have been placed as in FIG. 12, the virtual curved surface solid a including the inflow face 61 is first selected in step S600 of the path length deriving processing. Then, in step S610, virtual curved surface solids adjacent to or overlapping this virtual curved surface solid a are sequentially followed, with virtual curved surface solids b through f being selected. Of the selected virtual curved surface solids a through f, the virtual curved surface solid c includes the outflow face 62, so in step S620 determination is made that a virtual curved surface solid including the outflow face 62 has been reached. In step S650, the path length $L_f$ is derived based on the length of the line connecting the center points of the virtual curved surface solids on the path from the inflow face 61 to the outflow face 62. Specifically, this is derived as follows. First, the virtual curved surface solids a through c are on the path from the inflow face 61 to the outflow face 62, so the distance L1 between the center points of the virtual curved surface solids a and b, and the distance L2 between the center points of the virtual curved surface solids b and c, are derived. Next, the distance L0 from the inflow face 61 to the center of the virtual curved surface solid a, and the distance L3 from the outflow face 62 to the center of the virtual curved surface solid c, are derived. The total value of distance L0 through distance L3 is derived as the path length $L_f$. Note that the virtual curved surface solids d through f do not exist on the path from the inflow face 61 to the outflow face 62, and accordingly are unrelated to deriving of the path length $L_f$.

Figure 13:
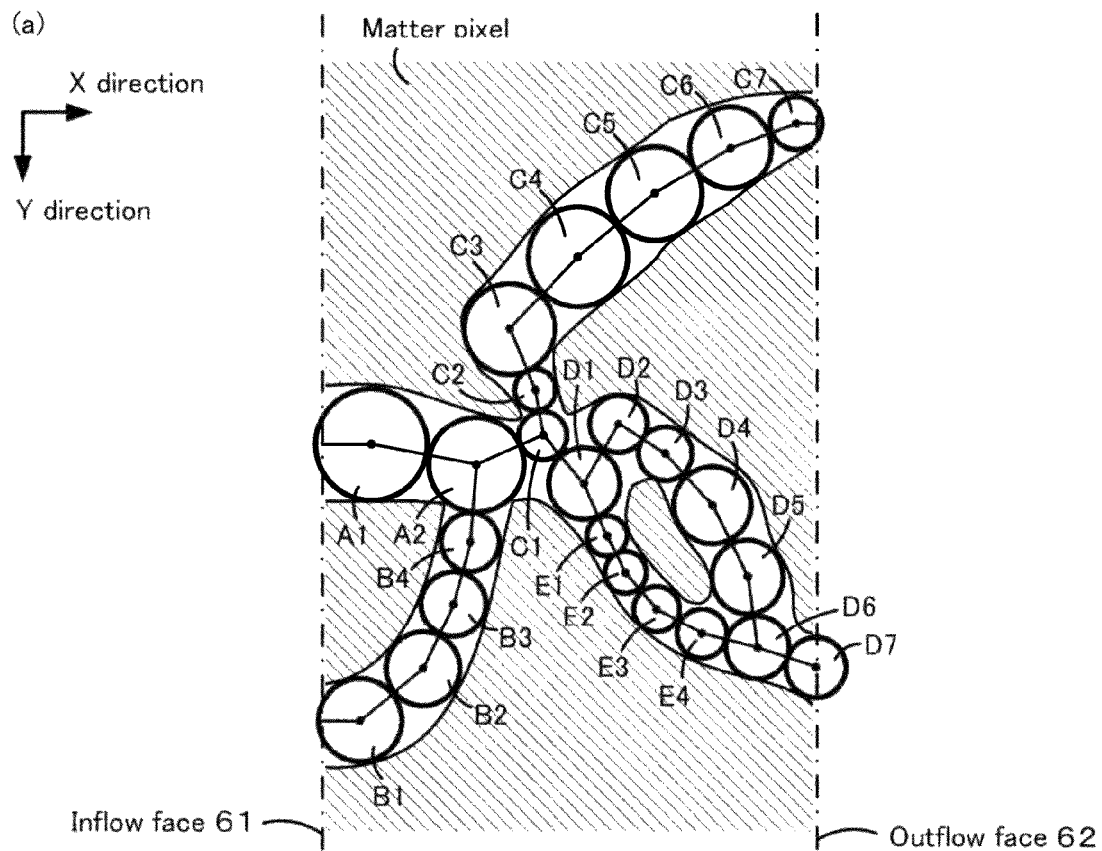
FIG. 13 is an explanatory diagram of deriving the path length $L_f$ in a case where a branch exists in the path from the inflow face 61 to the outflow face 62.
Figure 13:
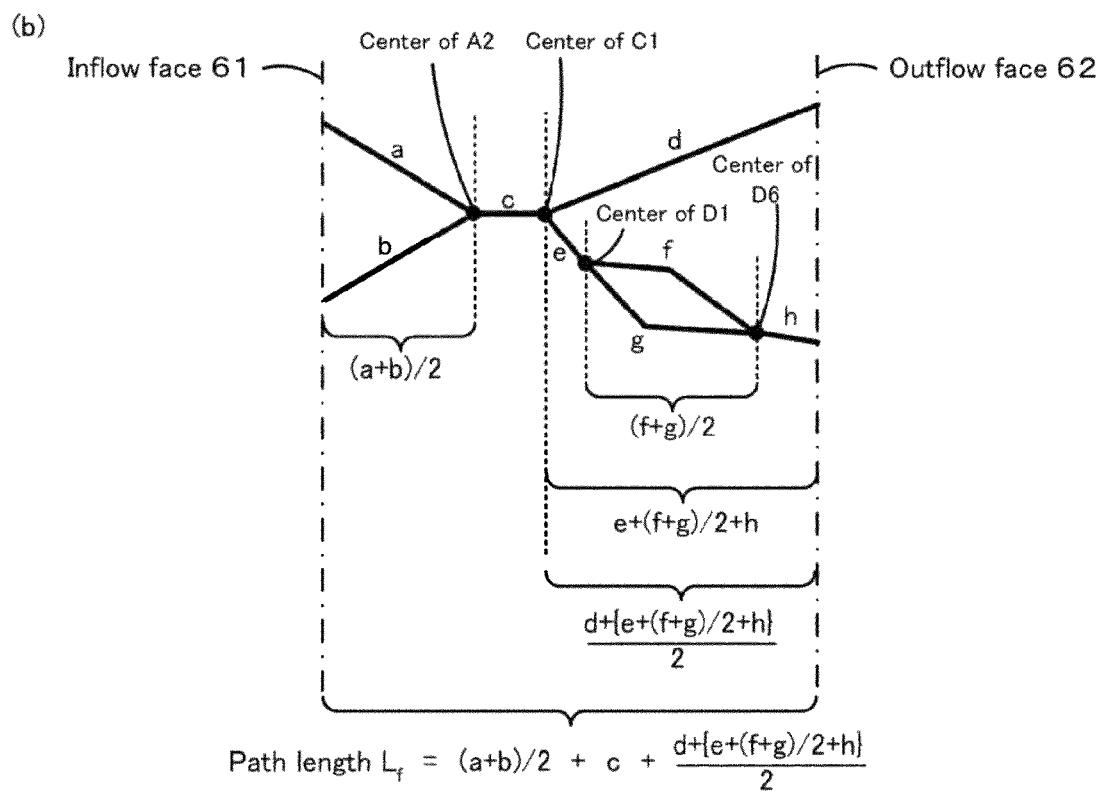

Note that when deriving the path length $L_f$, in the event that there are branches on the path from the inflow face 61 to the outflow face 62 made up of multiple virtual curved surface solids selected in steps S600 and S610, the average value of the multiple paths from the start of the branch to the end (merging point) is taken as the path length of the branching portion. A case where there are branches on the path include a case where there exists a path which branches off partway and merges again, a case where there exists a path which multiple virtual curved surface solids including the inflow face 61 merge, a case where there exists a path which branches off partway and multiple branches reach the outflow face 62 (there are multiple virtual curved surface solids reaching the outflow face 62), and so forth. FIG. 13 is an explanatory diagram of deriving a path length $L_f$ in the event that branches exist on the path from the inflow face 61 to the outflow face 62. FIG. 13(*a*) is an example of placement of a virtual curved surface solid in a case where branches exist on the path from the inflow face 61 to the outflow face 62. FIG. 13(*b*) is a schematic diagram of the path illustrated in FIG. 13(*a*) and is an explanatory diagram of deriving the path length $L_f$. Note that in FIG. 13(*a*), the virtual curved surface solids are represented by circles, for the sake of description. Let us say that there are virtual curved surface solids A1 through A2, B1 through B4, C1 through C7, D1 through D7, and E1 through E4, placed as illustrated in FIG. 13(*a*) and that the virtual curved surface solid A1 including the inflow face 61 is selected in step S600 of the path length deriving processing. In this case, in the subsequent step S610, virtual curved surface solids adjacent to or overlapping the virtual curved surface solid A1 are followed sequentially, with the virtual curved surface solids A2, B1 through B4, C1 through C7, D1 through D7, and E1 through E4 being selected. Of the selected virtual curved surface solids, the virtual curved surface solids C7 and D7 include the outflow face 62, so in step S620 determination is made that a virtual curved surface solid including the outflow face 62 has been reached. Now, branches exist on the path from the inflow face 61 to the outflow face 62 made up of the selected virtual curved surface solids. Specifically, there are a path following the virtual curved surface solids A1 and A2 in that order from the inflow face 61 and a path following the virtual curved surface solids B1 through B4 and A2 in that order from the inflow face 61, and these paths merge at the virtual curved surface solid A2. Also, after having following the virtual curved surface solids A2 and C1 in this order, the paths branch from the virtual curved surface solid C1 to the virtual curved surface solids C2 and D1. The path branching from virtual curved surface solid C1 to virtual curved surface solid C2 follows the virtual curved surface solids C2 through C7 in that order, and reaches the outflow face 62 at the virtual curved surface solid C7. The path branching from the virtual curved surface solid C1 to the virtual curved surface solid D1 further branches at the virtual curved surface solid D1 to the virtual curved surface solids D2 and E1. The path branching from the virtual curved surface solid D1 to the virtual curved surface solid D2 follows the virtual curved surface solids D2 through D6 in that order, the path branching from the virtual curved surface solid D1 to the virtual curved surface solid E1 follows the virtual curved surface solids E1 through E4 and D6 in that order, and merge at the virtual curved surface solid D6. The path then follows from the virtual curved surface solid D6 to the virtual curved surface solid D7 and reaches the outflow face 62. Deriving the path length $L_f$ in step S650 in the event that branches exist on the path from the inflow face 61 to the outflow face 62 will be described with reference to FIG. 13(b). In step S650, first, the path is sectioned into multiple sections at branching points and merging points, and the path length of each section is derived. Here, in FIG. 13(b) the paths in FIG. 13(a) are illustrated in a simplified manner, with the lengths a through h illustrated in FIG. 13(b) representing the path length of each section. The length a is the path length of the section from the inflow face 61 through the virtual curved surface solid A1 to the virtual curved surface solid A2 which is the merging point. The length b is the path length of the section from the inflow face 61 through the virtual curved surface solids B1 through B4 to the virtual curved surface solid A2 which is the merging point. The length c is the path length of the section from the virtual curved surface solid A2 which is the merging point to the virtual curved surface solid C1 which is the branching point. The length d is the path length of the section from the virtual curved surface solid C1 which is the branching point through the virtual curved surface solids C2 through C7 and reaching to the outflow face 62. The length e is the path length of the section from the virtual curved surface solid C1 which is the branching point to the virtual curved surface solid D1 which is the next branching point. The length f is the path length of the section from the virtual curved surface solid D1 which is the branching point through the virtual curved surface solids D2 through D5 to the virtual curved surface solid D6 which is the merging point. The length g is the path length of the section from the virtual curved surface solid D1 which is the branching point through the virtual curved surface solids E1 through E4 to the virtual curved surface solid D6 which is the merging point. The length h is the path length of the section from the virtual curved surface solid D6 which is the merging point through the virtual curved surface solid D7 and reaching to the outflow face 62. Note that the path lengths of each of the sections (lengths a through h) are derived based on the length of lines connecting the center points of the virtual curved surface solids, the length from the inflow face 61 to the center point of a virtual curved surface solid including the inflow face 61, and the length from the outflow face 62 to the center point of a virtual curved surface solid including the outflow face 62, as described with FIG. 12. Deriving the path lengths of each section in this way the path length $L_f$ is derived based on the path length of each section. Specifically, the path length of portions where multiple sections exist in parallel are taken as the average value of the path lengths of each section existing in parallel. Also, the path length of portions where multiple sections exist serially is the sum of the path length of each section existing serially. Thus, the path lengths of sections existing in parallel and the path length of sections existing serially are combined, and finally the path length $L_f$ from the inflow face 61 to the outflow face 62 is derived. For example, in FIG. 13(b), there are two sections existing in parallel from the inflow face 61 to the virtual curved surface solid A2 which is the merging point, and the lengths of these sections are length a and length b, so the average length thereof (a+b)/2 is taken as the path length from the inflow face 61 to the virtual curved surface solid A2. There are two sections existing in parallel from the virtual curved surface solid D1 which is the branching point to the virtual curved surface solid D6 which is the merging point, and the lengths of these sections are length f and length g, so the average length thereof (f+g)/2 is taken as the path length from the virtual curved surface solid D1 to the virtual curved surface solid D6. The section from the virtual curved surface solid C1 which is the branching point to the virtual curved surface solid D1 which is the next branching point, the section from the virtual curved surface solid D1 to the virtual curved surface solid D6 which is the merging point, and the section from the virtual curved surface solid D6 to the outflow face 62, exist serially, and the lengths of the sections are length e, length (f+g)/2, length h, so the sum of length thereof e+(f+g)/2+h is taken as the length of the section from the virtual curved surface solid C1 through the virtual curved surface solid D7 reaching the outflow face 62. There are two sections existing in parallel from the virtual curved surface solid C1 reaching to the outflow face 62, with the lengths of each section being length d and length e+(f+g)/2+h, so the average length thereof [d+{e+(f+g)/2+h}]/2 is taken as the path length of the section from the virtual curved surface solid C1 to the outflow face 62. The section from the inflow face 61 to the virtual curved surface solid A2, the section from the virtual curved surface solid A2 to the virtual curved surface solid C1, and the section from the virtual curved surface solid C1 to the outflow face 62, exist serially, and the lengths of each of the sections are length (a+b)/2, length c, and length [d+{e+(f+g)/2+h}]/2, so the sum of length thereof (a+b)/2+c+[d+{e+(f+g)/2+h}]/2 is taken as the path length from the inflow face 61 to the outflow face 62, i.e., the path length $L_f$. By deriving the path length $L_f$ in this way, even in cases where there are branches on the path from the inflow face 61 to the outflow face 62, the path length $L_f$ taking into consideration the branches can be derived. Note that the path length $L_f$ may be derived by other techniques, unrestricted to this.

With the path length $L_f$ derived in this way, the simpler the fluid path from the inflow face 61 to the outflow face 62 is (the closer to a straight line), the closer the value is to the distance L between the inflow face 61 and the outflow face 62. Also, the more complicated the fluid path from the inflow face 61 to the outflow face 62 is, the greater the value is as compared to the distance L between the inflow face 61 and the outflow face 62. Accordingly, the average value $L_{fmean}$ of multiple path lengths $L_f$ is a numerical value relating to the complexity of fluid paths (difficulty of fluid to flow) for the overall porous body, when a fluid flows through the space inside the porous body.

By deriving the pressure drop index $P_e$ in this way, the pressure drop index $P_e$ is a value having a high correlation of the actual pressure drop of the porous body. Accordingly, by deriving this pressure drop index $P_e$, the pressure drop property of the porous body can be predicted and evaluated more precisely, for example. Also, the pressure drop evaluation module 25f may perform evaluation of the pressure drop property of the porous body by determining whether the value of the pressure drop index $P_e$ is at or below a predetermined threshold, or the like, to derive evaluation results as well. Further, the pressure drop evaluation module 25f may analyze the microstructure of the porous body by deriving the pressure drop $P_S$ per unit thickness of the porous body by $P_S$=constant $\alpha \times P_e^2$+constant $\beta \times P_e$. The pressure drop $P_S$ per unit thickness of the porous body derived from the pressure drop index $P_e$ in this way approximately matches the actual pressure drop of the porous body. Accordingly, the pressure drop property of the porous body can be predicted or evaluated more precisely, by deriving this pressure drop $P_S$ as microstructure analysis. Also, the pressure drop evaluation module 25f may evaluate the pressure drop property of the porous body by determining whether or not the pressure drop $P_S$ is at or below a predetermined threshold, or the like. Note that the constant α is a positive number and the constant β is a real number. Also, pressure drop $P_S$>0 holds within the range of pressure drop index $P_e$>0. Also, constant α and constant β may be obtained by experiment for example, so that the pressure drop $P_S$ and the actual pressure drop of the porous body match more precisely.

EXAMPLES

Hereinafter, examples of actually creating the analysis processing program and microstructure analysis device will be described as Examples.

Example 1

As Example 1, an analysis processing program having the functions of the above-described embodiment was created. This program was then stored in the HDD of a computer having a controller including a CPU, ROM, and RAM, and a HDD, thereby yielding a microstructure analysis device according to Example 1.

[Output of Tabulation Results of Pore Diameter]

Figure 14:
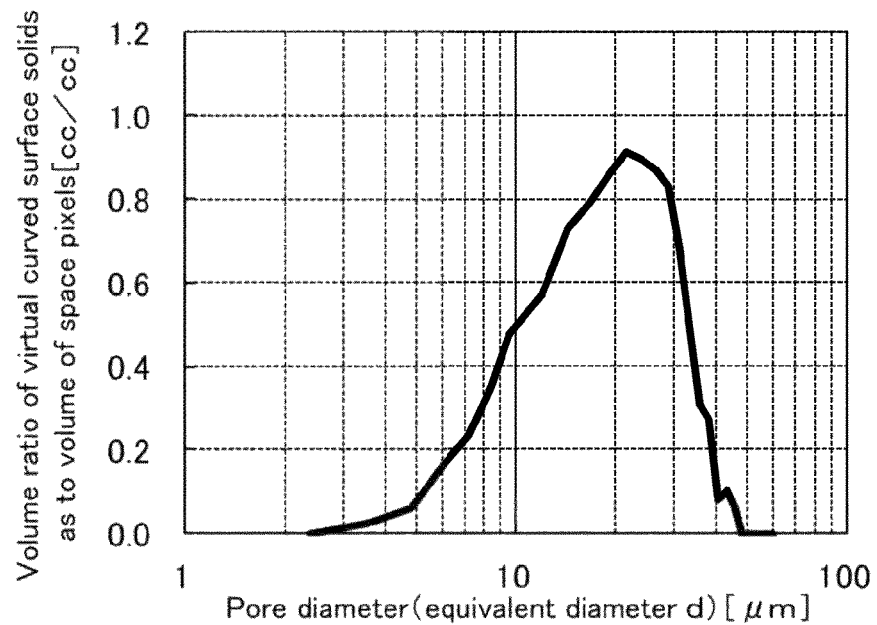
FIG. 14 is a graph illustrating tabulation results of pore diameter (equivalent diameter d) of a porous body 1.

A plastic green body was fabricated by mixing SiC powder and metal Si powder at a ratio of 80:20 by mass, adding starch and foamed plastic as pre-forming agents, and further adding methylcellulose, hydroxypropoxyl methylcellulose, a surfactant, and water. This green body was formed by extrusion to the form illustrated in FIGS. 2 and 3, and dried by microwave and heated air to yield a compact body. This compact body was degreased at approximately 400° C. in atmosphere, and thereafter fired at approximately 1450° C. in an Ar inactive atmosphere, thereby yielding a porous body 1 serving as the porous partition 44. Also, of pixel data obtained by performing a CT scan of the porous body 1, one data was extracted where the X direction is 300 μm (=1.2 μm×250 pixels) which is the same value as the thickness in the direction of exhaust gas passing direction, the Y direction is 480 μm (=1.2 μm×400 pixels), and the Z direction is 480 μm (=1.2 μm×400 pixels), which was stored in the HDD as the above-described porous body data 60, and the above-described analysis processing routine was executed regarding this porous body data 60. Analysis result data including the above-described porous body table, virtual curved surface solid table, and the values of equivalent diameter d and volume V of each virtual curved surface solid, was then obtained. FIG. 14 is a graph illustrating tabulation results of the pore diameter (equivalent diameter d) of the porous body 1 based on this analysis result data. FIG. 14 is a log differential pore volume distribution graph with the horizontal axis as the equivalent diameter d, and the vertical axis as the volume ratio [cc/cc] as to the volume of space pixels (=(the sum of volumes V of virtual curved surface solids corresponding to the equivalent diameters d)/(sum of volume of all space pixels)). It can be seen that with the microstructure analysis device, the equivalent diameters d of the placed virtual curved surface solids are derived, and the distribution of pore diameters within the porous body can be analyzed as a distribution of equivalent diameters d in the porous body by using this value, as illustrated in the drawings.

[Evaluation by Equivalent Diameter d]

Figure 15:
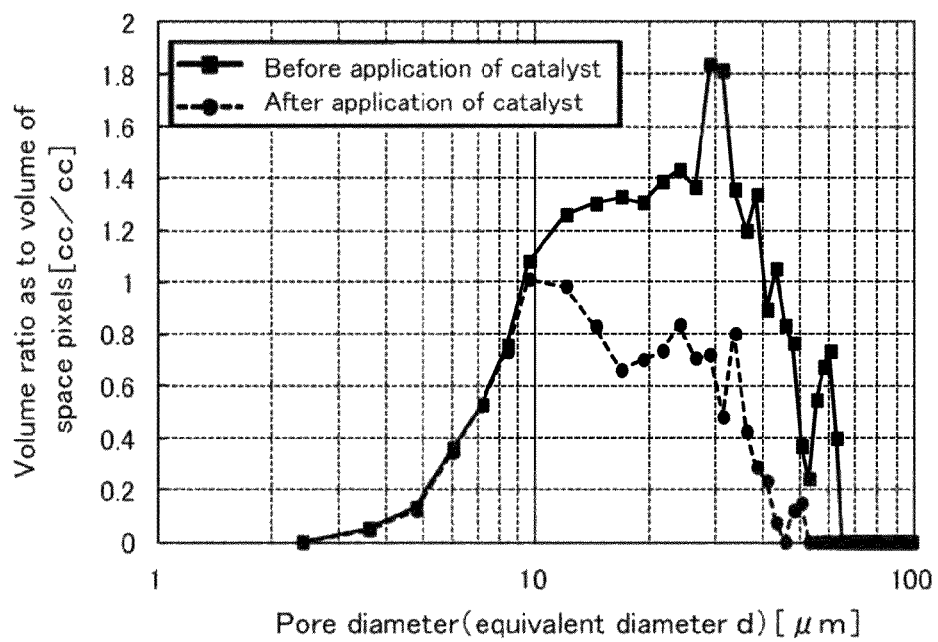
FIG. 15 is a graph illustrating tabulation results of pore diameter (equivalent diameter d) of a porous body 2 after application of a catalyst.

A porous body 2 tending to have greater pore diameter as compared to the porous body 1 was created using the same material and manufacturing process as with the porous body 1 described above. Of pixel data obtained by performing a CT scan of the porous body 2, one data was extracted where the X direction is 300 μm, the Y direction is 480 μm, and the Z direction is 480 μm, which was stored in the HDD as the above-described porous body data 60, in the same way as with the porous body 1, and the above-described analysis processing routine was executed regarding the porous body data 60 of this porous body 2. Analysis result data including the above-described porous body table, virtual curved surface solid table, and the values of equivalent diameter d and volume V of each virtual curved surface solid, was then obtained. Also, a catalyst was applied to the porous body 2, and porous body data 60 was created regarding the porous body 2 after application and the above-described analysis processing routine was performed. FIG. 15 is a graph illustrating tabulation results of the pore diameter (equivalent diameter d of the virtual curved surface solid) of the porous body 2 based on the analysis result data before and after application of the catalyst. The vertical axis and horizontal axis in FIG. 15 are the same as with FIG. 14. In FIG. 15, the volume ratio of virtual curved surface solids of which the equivalent diameter d exceeds 10 μm occupying as to the volume of space pixels has decreased after application of the catalyst as compared to before. On the other hand, the volume ratio of virtual curved surface solids of which the equivalent diameter d is 10 μm or smaller occupying as to the volume of space pixels exhibits little change before and after application. The cause of this can be thought to be that the catalyst was not applied to portions where virtual curved surface solids with equivalent diameter d of 10 μm or smaller were placed, and there was little change in volume before and after application of the catalyst. Accordingly, it can be conceived that the volume ratio of virtual curved surface solids with equivalent diameter d of 10 μm or smaller is preferably small. For example, the volume ratio of virtual curved surface solids with equivalent diameter of 10 μm or smaller is preferably 25% or less.

Note that application of the catalyst was performed as follows. First, alumina:platinum:ceria material were mixed at a predetermined mass ratio, and a catalyst slurry with water as a solvent was prepared. Next, the outlet edge face of the honeycomb filter (side where exhaust gas flows out) was dipped to a predetermined height, and suctioning was performed from the inlet edge face (side where exhaust gas flows in) for a predetermined time while adjusting to a predetermined suction pressure and suction flow, so that the catalyst was carried on the partitions, dried at 120° C. for two hours, and baked at 550° C. for one hour. The amount of catalyst per unit volume of the honeycomb filter was set to 30 g/L.

[Evaluation of Collection Performance by Spatial Uniformity Index γ]

Figure 16:
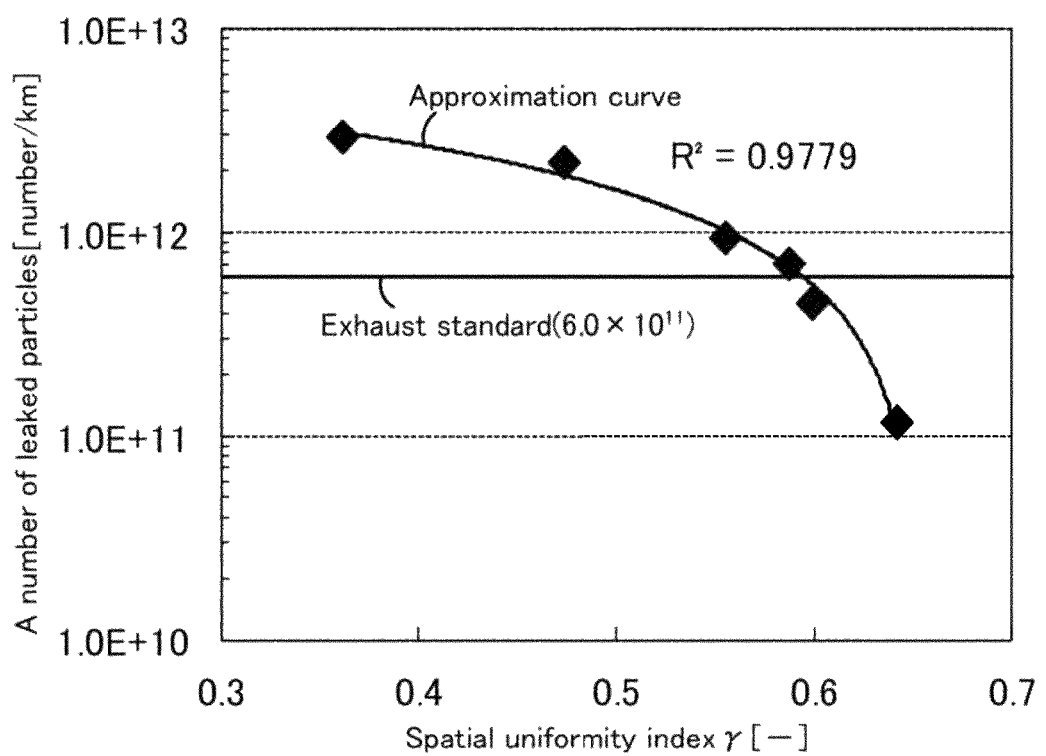
FIG. 16 is a graph illustrating the relation between spatial uniformity index $\gamma$ and the number of leaked particles with porous bodies 3 through 8.

Porous bodies 3 through 8 were created using the same material and manufacturing process as with the porous body 1 described above. Of pixel data obtained by performing a CT scan of each of the porous bodies 3 through 8, one data was extracted where the X direction is 300 μm, the Y direction is 480 μm, and the Z direction is 480 μm, which was stored in the HDD as the above-described porous body data 60, in the same way as with the porous body 1, and the above-described analysis processing routine was executed regarding this porous body data 60 of the porous bodies 3 through 8. Analysis result data including the spatial uniformity index γ was obtained as analysis result data. A fluid including particulate material was passed through the porous bodies 3 through 8, the remainder of particulate material in the fluid following passage was measured as the number of leaked particles, and the number of leaked particles converted into the number of particles leaked per 1 km of passage distance [number/km] as obtained as a value indicating collecting performance. FIG. 16 is a graph illustrating the relation between the spatial uniformity index γ obtained by the microstructure analysis device and the number of leaked particles actually measured for the porous bodies 3 through 8. As illustrated in the diagram, it can be seen that the greater the spatial uniformity index γ is, the smaller the number of leaked particles tends to be (the collecting performance is high). Also, it is conceivable to predict the number of leaked particles from the spatial uniformity index γ by using an approximation curve based on points plotted in the diagram. For example, if the spatial uniformity index γ is 0.6 or greater from the approximation curve, it can be understood that conditions of leaked particles of $6.0 \times 10^{11}$ or less which is an exhaust gas restriction value for automobiles (Euro 6) are satisfied, so it can be thought to be possible to determine acceptability of collecting performance based on whether or not the spatial uniformity index γ is 0.6 or greater. Note that while there are cases where the spatial uniformity index γ changes due to application of the catalyst, the spatial uniformity index γ after application of the catalyst is preferably 0.5 or higher.

[Evaluation by Pressure Drop P]

Figure 17:
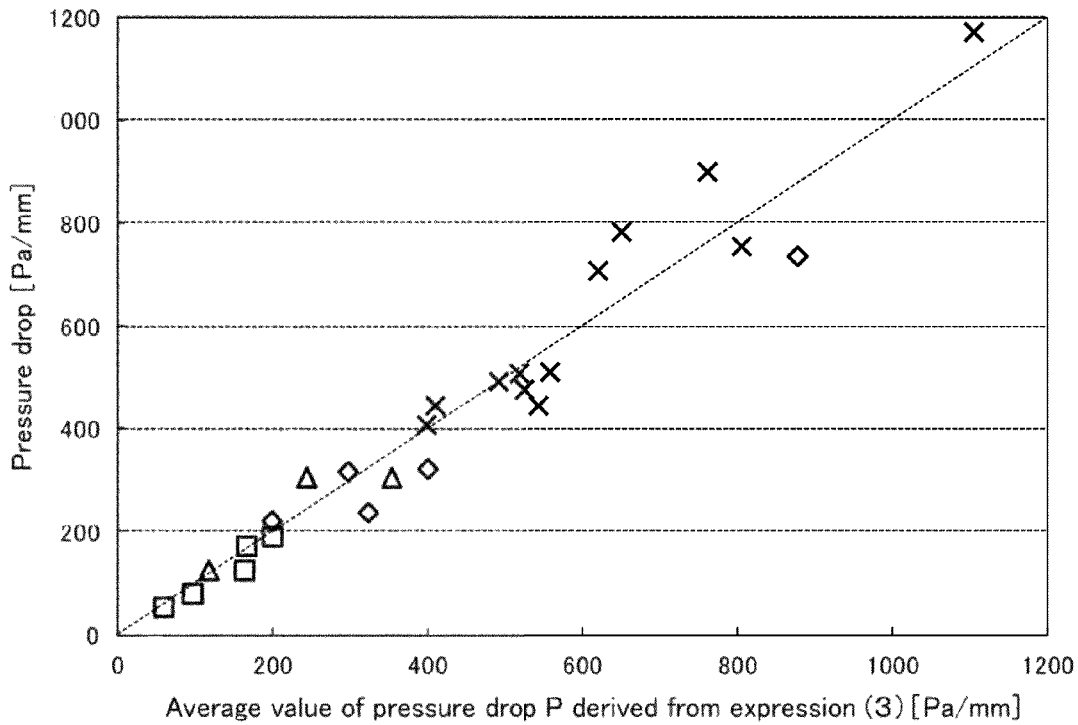
FIG. 17 is a graph illustrating the relation between the average value of pressure drop P derived with Expression (3) and pressure drop by the lattice Boltzmann method.
Figure 18:
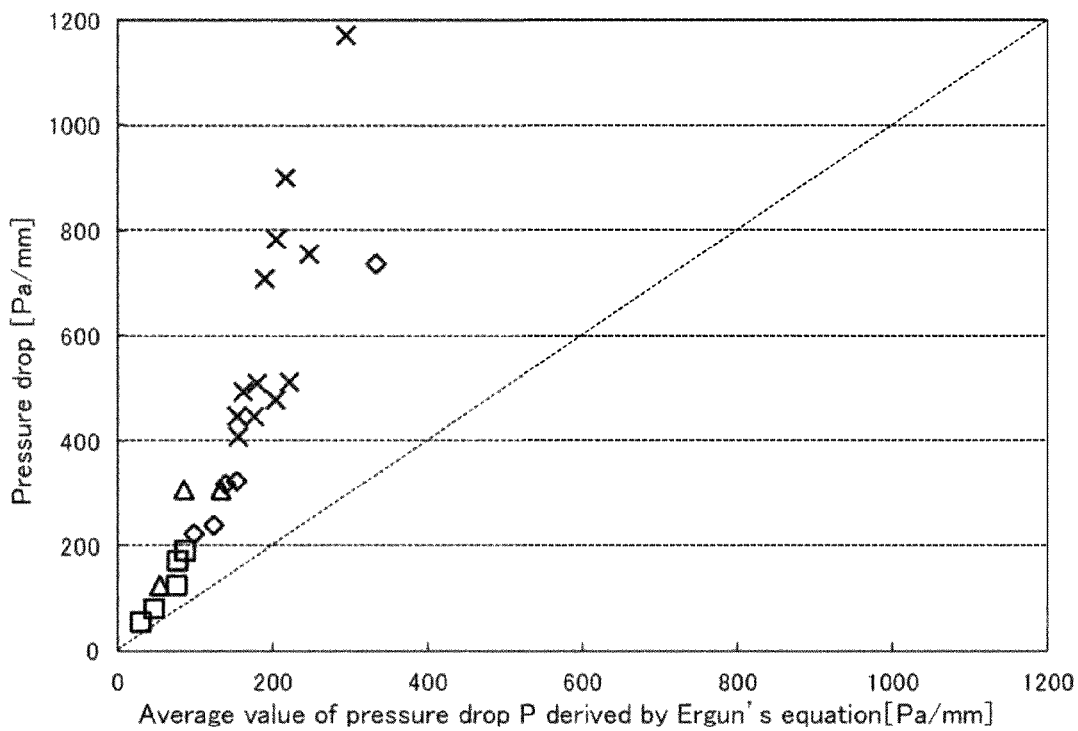
FIG. 18 is a graph illustrating the relation between the average value of pressure drop P derived by Ergun's Equation and pressure drop by the lattice Boltzmann method.

Porous bodies 9 through 12 were created using the same material and manufacturing process as with the porous body 1 described above. Of pixel data obtained by performing a CT scan of the porous body 9 through 12, one data was extracted where the X direction is 300 μm, the Y direction is 480 μm, and the Z direction is 480 μm, which was stored in the HDD as the above-described porous body data 60, in the same way as with the porous body 1, and the above-described analysis processing routine was executed regarding this porous body data 60 of porous bodies 9 through 12. Data including the average value of pressure drop P was obtained. Also, for comparison, the average value of the pressure drop P was derived with a method the same as with the microstructure analysis device according to Example 1 except for using Ergun's Equation instead of the above-described Expression (3), for each of the porous bodies 9 through 12. Also, pressure drop of the porous body 9 through 12 was derived following a known method based on fluid analysis results by the lattice Boltzmann method (this pressure drop will be written as "pressure drop according to the lattice Boltzmann method" hereinafter). FIG. 17 is a graph illustrating the relation between the average value of pressure drop P derived from Expression (3) and pressure drop according to the lattice Boltzmann method, and FIG. 18 is a graph illustrating the relation between the average value of pressure drop P derived by Ergun's Equation and pressure drop according to the lattice Boltzmann method. From FIG. 17 and FIG. 18, it can be seen that the correlation with pressure drop according to the lattice Boltzmann method is greater with the average value of pressure drop P derived with Expression (3) as compared to the average value of pressure drop P derived by Ergun's Equation. Also, the higher the average value of the pressure drop P is, the greater the deviation between the average value of pressure drop P derived by Ergun's Equation and the pressure drop according to the lattice Boltzmann method is, but this tendency is not observed regarding the average value of pressure drop P derived by Expression (3), and a value close to the pressure drop according to the lattice Boltzmann method is indicated regardless of the magnitude of the average value of the pressure drop P. From this, it can be seen that the actual pressure drop can be predicted with good precision and pressure drop can be evaluated with good prediction based on the average value of pressure drop P derived by Expression (3). Also, with the pressure drop according to the lattice Boltzmann method obtained with the known method, while pressure drop can be derived, which microstructure features of the porous body were affecting increase or decrease in pressure drop could not be analyzed. On the other hand, with the results this time, the correlation between the pressure drop according to Expression (3) and pressure drop according to the lattice Boltzmann method was high, so it can be seen that increase or decrease in pressure drop according to the lattice Boltzmann method is affected by the parameters in Expression (3), and accordingly it can be understood from Expression (3) how which parameters should be adjusted to reduce the pressure drop. Accordingly, it has been found that the parameters of Expression (3) can be used as an index to manufacture a porous body with the desired pressure drop.

[Evaluation of Pressure Drop by In-Plane Uniformity Index $\gamma_x$]

Figure 19:
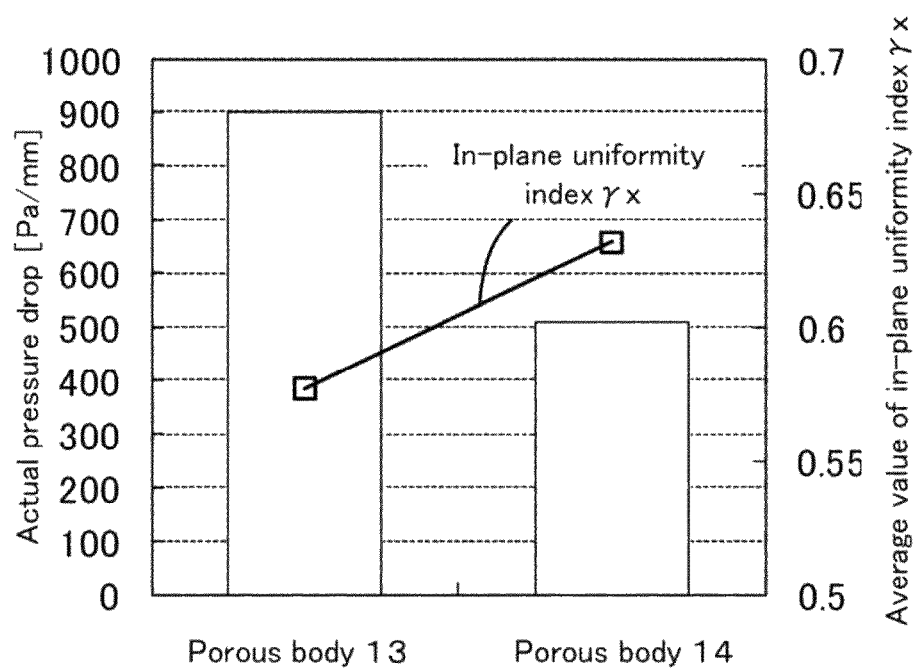
FIG. 19 is a graph illustrating the average value of in-plane uniformity index $\gamma_x$ and actual pressure drop with porous bodies 13 and 14.

Porous bodies 13 and 14 were created using the same material and manufacturing process as with the porous body 1 described above. Of pixel data obtained by performing a CT scan of the porous body 13 and 14, one data was extracted where the X direction is 300 μm, the Y direction is 480 μm, and the Z direction is 480 μm, which was stored in the HDD as the above-described porous body data 60, in the same way as with the porous body 1, and the above-described analysis processing routine was executed regarding this porous body data 60 of porous body 13 and 14. Data including the average value of in-plane uniformity index $\gamma_x$ was obtained as analysis result data. Also, for comparison, the average value of pressure drop P was derived by the same method as with the microstructure analysis device according to Example 1 except for the point of using Ergun's Equation instead of the above-described Expression (3), using the same porous body data as above, for each of the porous bodies 13 and 14. As a result, the average value of pressure drop P in the case of using Ergun's Equation was approximately the same value in the porous bodies 13 and 14. Also, the actual pressure drop of the porous bodies 13 and 14 was measured according to a method described in the embodiments in Japanese Unexamined Patent Application Publication No. 2005-114612. FIG. 19 is a graph illustrating the average value of in-plane uniformity index $\gamma_x$ and actual pressure drop for the porous bodies 13 and 14. As can be seen from the diagram, there is difference between the porous bodies 13 and 14 regarding actual pressure drop, regardless of the average value of pressure drop P having been the same using Ergun's Equation. Also, the porous body 14 with the greater in-plane uniformity index $\gamma_x$ has a smaller value for actual pressure drop, so it can be seen that the greater the value of in-plane uniformity index $\gamma_x$ is, the better the pressure drop property tends to be. Also, from the actual values of pressure drop for the porous bodies 13 and 14, it can be conceived that the pressure drop property of the porous body is acceptable when the in-plane uniformity index $\gamma_x$ is 0.6 or greater.

[Evaluation by Flow-Through Velocity T]

Figure 20:
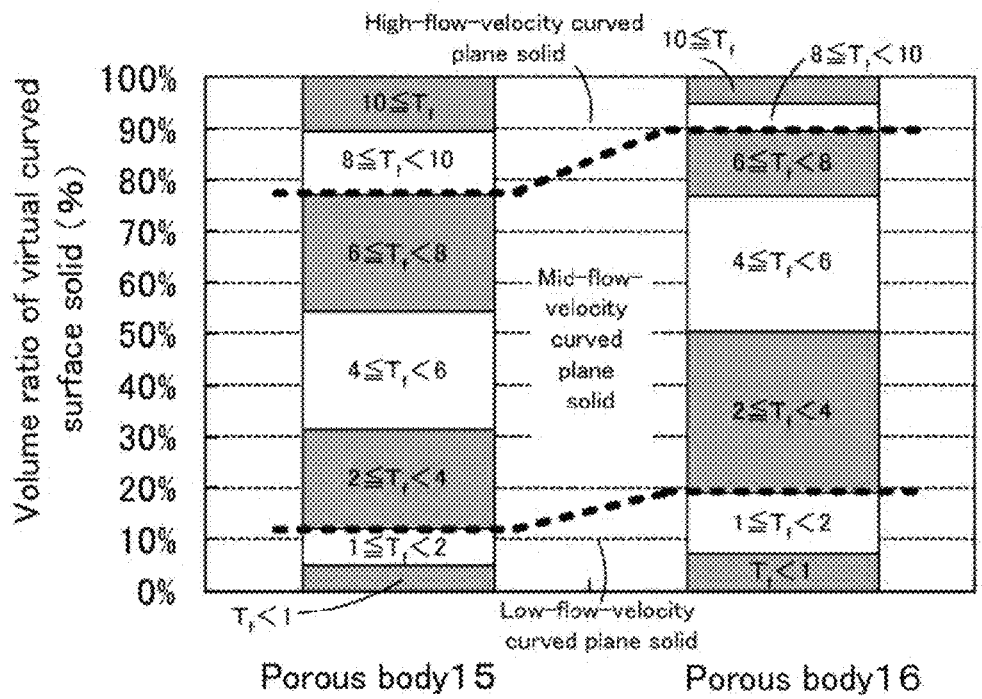
FIG. 20 is a graph illustrating virtual curved surface solids in porous bodies 15 and 16 being classified by flow velocity ratio $T_f(=T/T_{in})$.
Figure 21:
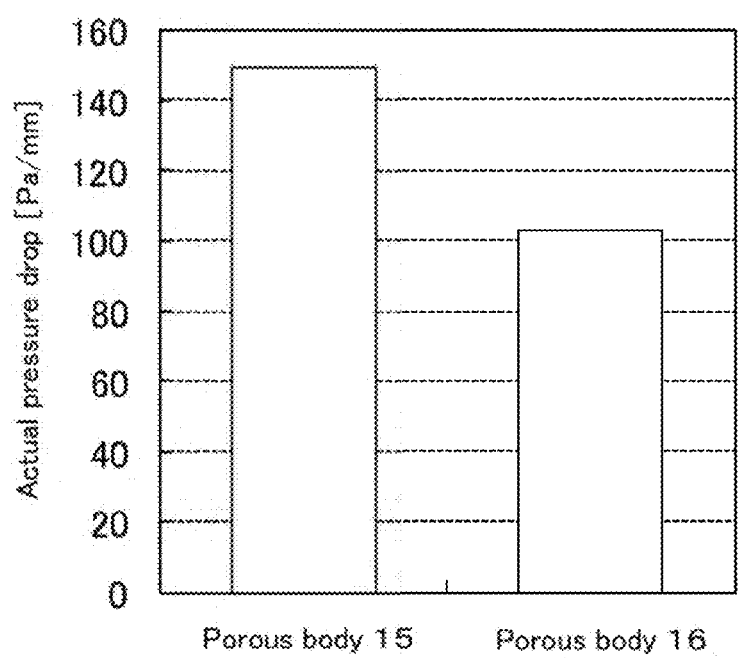
FIG. 21 is a graph illustrating actual pressure drop with porous bodies 15 and 16.

Porous bodies 15 and 16 were created using the same material and manufacturing process as with the porous body 1 described above. Of pixel data obtained by performing a CT scan of the porous body 15 and 16, one data was extracted where the X direction is 300 μm, the Y direction is 480 μm, and the Z direction is 480 μm, which was stored in the HDD as the above-described porous body data 60, in the same way as with the porous body 1, and the above-described analysis processing routine was executed regarding this porous body data 60 of porous body 15 and 16. Data including the volume V and flow velocity ratio $T_f(=T/T_{in})$ of each virtual curved surface solid was obtained as analysis result data. Also, the actual pressure drop of the porous bodies 15 and 16 was measured according to the method described in the embodiments in Japanese Unexamined Patent Application Publication No. 2005-114612. FIG. 20 is a graph illustrating the virtual curved surface solids in the porous bodies 15 and 16 having been classified by flow velocity ratio $T_f(=T/T_{in})$. FIG. 21 is a graph illustrating actual pressure drop of the porous bodies 15 and 16. Note that in FIG. 20, the virtual curved surface solids are classified by flow velocity ratio $T_f$, the total value of volume V is derived for virtual curved surface solids of the same classification, the percentage of the total value of volume V for the virtual curved surface solids of each classification as to the total value of volume V of all virtual curved surface solids is obtained, and this percentage is the vertical axis. From FIG. 20 and FIG. 21, it can be seen that the porous body 16 of which the volume ratio of high-flow-velocity curved surface solids is small has smaller actual pressure drop, and accordingly the pressure drop property tends to be acceptable. Also, while the volume ratio of low-flow-velocity curved surface solids is 20% or less and the volume ratio of high-flow-velocity curved surface solids is 10% or less with the porous body 16, the volume ratio of low-flow-velocity curved surface solids is 20% or less but the volume ratio of high-flow-velocity curved surface solids exceeds 10% with the porous body 15. Accordingly, it can be conceived that performance of the porous body is acceptable with a volume ratio of high-flow-velocity curved surface solids of 10% or less. Also, it can be conceived that the volume ratio of low-flow-velocity curved surface solids of 20% or less and the volume ratio of high-flow-velocity curved surface solids of 10% or less is even more preferable.

[Results of Classification by Equivalent Diameter d]

Figure 22:
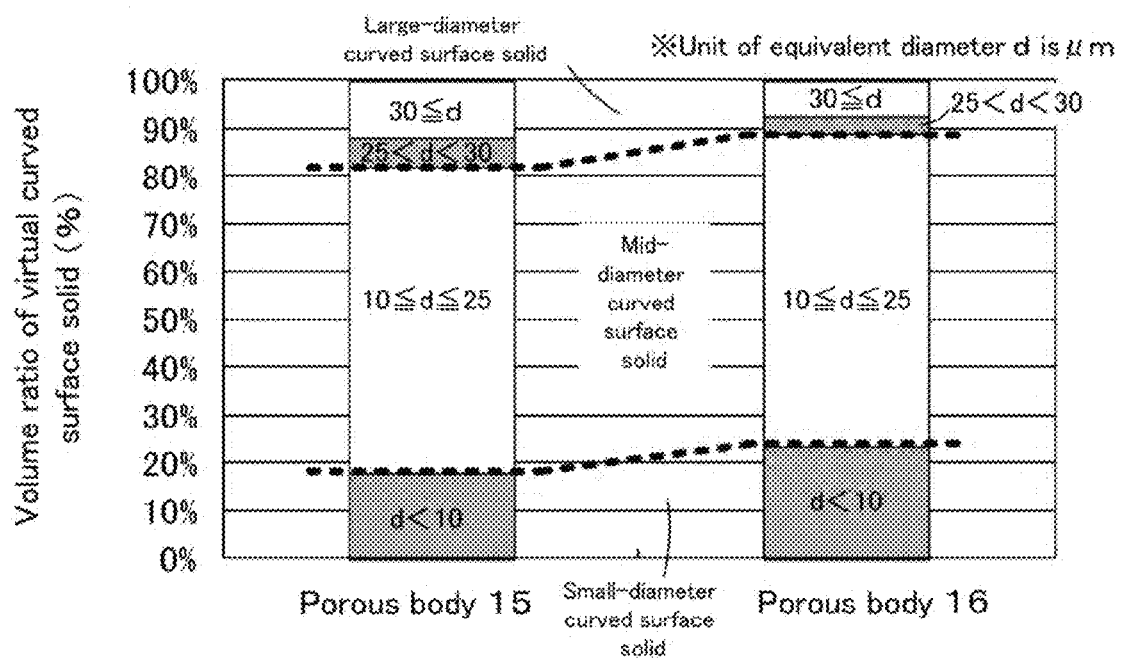
FIG. 22 is a graph illustrating virtual curved surface solids in porous bodies 15 and 16 being classified by equivalent diameter d.

Equivalent diameter d and volume V values for the virtual curved surface solids of the porous bodies 15 and 16, and classification result data of the virtual curved surface solids thereby, were obtained from analysis result data obtained by executing the analysis processing routine on the porous bodies 15 and 16 described above. FIG. 22 is a graph illustrating the way in which the virtual curved surface solids of analysis date with the porous bodies 15 and 16 were classified by the equivalent diameter d of the virtual curved surface solids. Note that in FIG. 22, the virtual curved surface solids are classified by equivalent diameter d, the total value of volume V is derived for virtual curved surface solids of the same classification, the percentage of the total value of volume V for the virtual curved surface solids of each classification as to the total value of volume V of all virtual curved surface solids is obtained, and this percentage is the vertical axis. As illustrated in the diagram, with the porous bodies 15 and 16, the volume ratio of mid-diameter curved surface solids (virtual curved surface solids of 10 µm≤equivalent diameter d≤25 µm) was 60% or greater in either case. Also, the porous body 16 of which the volume ratio of mid-diameter curved surface solids was greater had smaller pressure drop (see FIG. 21), and the performance of the porous body tended to be better. The volume ratio of small-diameter curved surface solids (virtual curved surface solids with equivalent diameter d<10 µm) was 25% or less in either case of porous bodies 15 and 16. Note that as another classification method, when virtual curved surface solids of 30 µm≤equivalent diameter d were classified as large-diameter curved surface solids, the volume ratio of large-diameter curved surface solids exceeded 10% for the porous body 15, but was less than 10% for the porous body 16, as can be seen from FIG. 22. From this, and the values of actual pressure drop in FIG. 21, it can also be conceived that the performance of porous bodies is more acceptable with a volume ratio of 10% or less for virtual curved surface solids of 30 µm≤equivalent diameter d.

Example 2

An analysis processing program having the same functions as with Example 1, except for the point of mutual overlapping of virtual curved surface solids being permitted, and pressure drop index $P_e$ being derived instead of pressure drop P, was created. This program was then stored in the HDD of a computer having a controller including a CPU, ROM, and RAM, and a HDD, thereby yielding a microstructure analysis device according to Example 2.

[Evaluation by Pressure Drop Index $P_e$]

Figure 23:
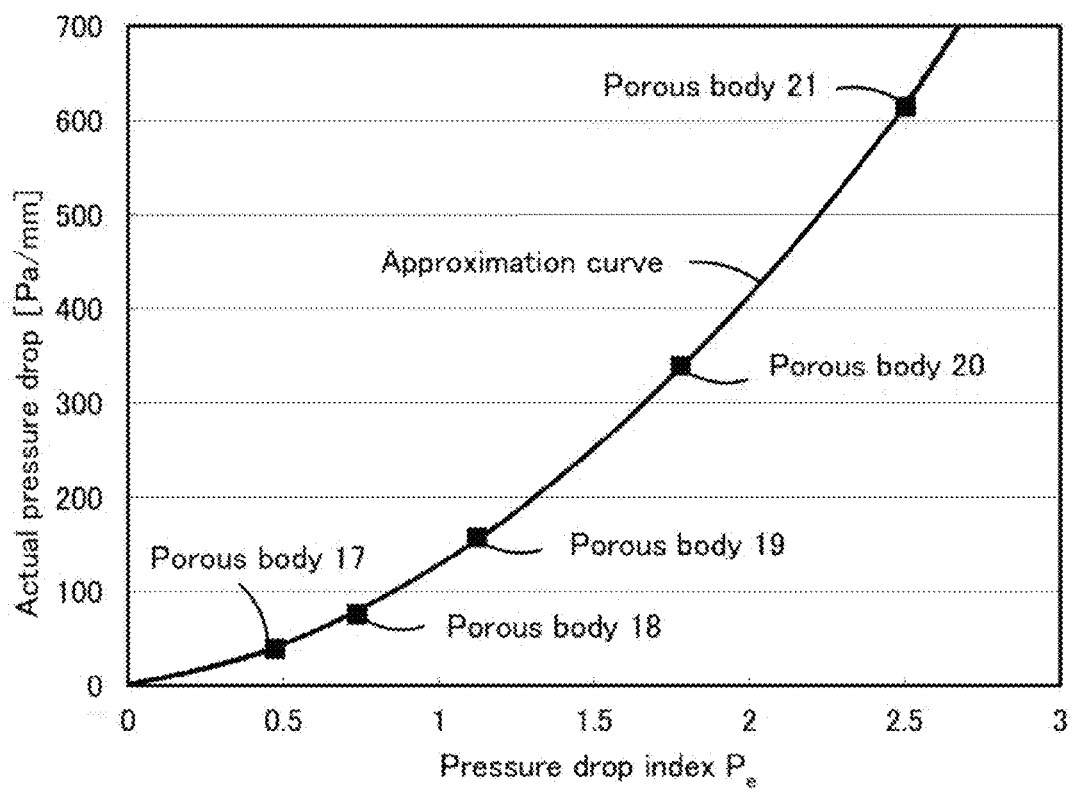
FIG. 23 is a graph illustrating the relation between pressure drop index $P_e$ and actual pressure drop with porous bodies 17 through 21.

Porous bodies 17 through 21 were created using the same manufacturing process as with the porous body 1 described above, with material changed as appropriate from those of the porous body 1. Of pixel data obtained by performing a CT scan of the porous bodies 17 through 21, one data was extracted where the X direction is 300 µm, the Y direction is 480 µm, and the Z direction is 480 µm, which was stored in the HDD as the above-described porous body data 60, in the same way as with the porous body 1, and the above-described analysis processing routine was executed regarding this porous body data 60 of porous bodies 17 through 21. Analysis result data including pressure drop index $P_e$ was obtained as analysis result data. Note that regarding deriving of the pressure drop index $P_e$, the predetermined number of step S660 of the path length deriving processing in FIG. 11 (the number of path lengths $L_f$ to be derived) was set to the value 1000. Also, the actual pressure drop of the porous bodies 17 through 21 (pressure drop per unit thickness [Pa/mm]) was measured according to the method described in the embodiments in Japanese Unexamined Patent Application Publication No. 2005-114612. FIG. 23 is a graph illustrating the relation between the pressure drop index $P_e$ and actual pressure drop of the porous bodies 17 through 21. Note that the curve in the drawing is an approximation curve where points illustrating the relation of pressure drop index $P_e$ and actual pressure drop of the porous bodies 17 through 21 have been plotted, and the approximation curve is derived from these five points. From the plotted points and the approximation curve, it can be found that the actual pressure drop of the porous bodies can be expressed as a quadratic function of pressure drop index $P_e$ passing through the origin. That is to say, it has been found that with pressure drop $P_S$=constant $\alpha \times P_e^2$+constant $\beta \times P_e$ using the pressure drop index $P_e$ of the porous bodies 17 through 21, the pressure drop $P_S$ and actual pressure drop approximately match. Note that the determination coefficient $R^2$ obtained from the approximation curve in FIG. 23 (actual pressure drop=constant $\alpha \times P_e^2$+constant $\beta \times P_e$) and the five plotted points was the value 0.999. From the above, it has been found that the actual pressure drop of the porous body can be precisely predicted and evaluated by deriving pressure drop index $P_e$. Also, it has been round that by deriving the pressure drop $P_S$ by $P_S$=constant $\alpha \times P_e^2$+constant $\beta \times P_e$, a value approximately the same as the actual pressure drop can be derived as the pressure drop $P_S$. Further, since the materials of the porous bodies 17 through 21 differ from each other, it has been found that prediction and evaluation of pressure drop using pressure drop index $P_e$ can be performed regardless of the material of the porous body.

The present application claims priority from Japanese Patent Application No. 2012-082540 filed on Mar. 30, 2012, the entire contents of which are incorporated herein by reference.

INDUSTRIAL APPLICABILITY

The present invention is applicable to the manufacturing industry of porous bodies used as filters for purging exhaust gas emitted from stationary engines and burning appliances and the like for automobiles, construction equipment, and industrial use.

REFERENCE SIGNS LIST 20 user personal computer (PC), 21 controller, 22 CPU, 23 ROM, 24 RAM, 25 HDD, 25a analysis processing program, 25b virtual curved surface solid placement module, 25c fluid analyzing module, 25d in-plane uniformity index evaluation module, 25e spatial uniformity index evaluation module, 25f pressure drop evaluation module, 25g flow-through velocity evaluation module, 25h equivalent diameter evaluation module, 25i analysis result output module, 26 display, 27 input device, 30 honeycomb filter, 32 external protective portion, 34 cell, 36 inlet-opened cell, 36a inlet, 36b outlet, 38 outlet sealant, 40 outlet-opened cell, 40a inlet, 40b outlet, 42 inlet sealant, 44 porous partition, 50 region, 60 porous body data, 61 inflow face, 62 outflow face, 63 X-Y plane, 64 enlarged drawing, 71 porous body table, 72 inflow/outflow table, 80 porous body data, 81 porous body table, 82 inflow/outflow table, 83 curved surface solid table, 85 virtual wall face

The invention claimed is:

1. A microstructure analysis method of a porous body using porous body data in which correlated position information representing position of a pixel obtained by a 3 dimensional scan of the porous body, and pixel type information representing whether a space pixel representing that the pixel is space or a matter pixel representing that the pixel is matter, comprising;
   (a) a step to take a curved surface solid including a parent virtual sphere and one or more child virtual spheres with which a portion of pixels occupied by the parent virtual sphere overlap as a virtual curved surface solid, and place the multiple virtual curved surface solids so as to fill in the space pixels with curved surface solid pixels which are pixels occupied by the virtual curved surface solid, referencing the porous body data; and
   (b) a step to analyze microstructure of the porous body based on information relating to virtual curved surface solids placed in the step (a).

2. The microstructure analysis method according to claim 1, wherein in the step (a), the virtual curved surface solid is placed such that the center of the child virtual sphere configuring the virtual curved surface solid overlaps with the parent virtual sphere configuring the virtual curved surface solid.

3. The microstructure analysis method according to claim 1, wherein in the step (a), the multiple virtual curved surface solids are placed permitting the virtual curved surface solids to overlap with each other.

4. The microstructure analysis method according to claim 1, wherein in the step (a), the multiple virtual curved surface solids are placed so that the virtual curved surface solids do not overlap with each other.

5. The microstructure analysis method according to claim 1, wherein in the step (a), the virtual curved surface solids are placed so that the curved surface solid pixels do not overlap with the matter pixels.

6. The microstructure analysis method according to claim 1, wherein in the step (a), processing to place one of the virtual curved surface solids is performed by placing the parent virtual sphere having the greatest spherical diameter that can be placed so as to fill in the space pixels, and placing one or more of the child virtual spheres such that pixels occupied by the child virtual spheres partially overlap with pixels occupied by the placed parent virtual sphere and fill in the space pixels, and the multiple virtual curved surface solids are placed by repeating this processing so that virtual curved surface solids are placed in mutually different positions.

7. The microstructure analysis method according to claim 1, wherein in the step (a), processing to place one of the virtual curved surface solid is performed by placing the parent virtual sphere having the greatest spherical diameter that can be placed so as to fill in the space pixels without overlapping with the matter pixels, and placing one or more of the child virtual spheres such that the center of the child virtual spheres overlaps with the placed parent virtual sphere, and such that pixels occupied by the child virtual spheres do not overlap with the matter pixels and fill in the space pixels, and the multiple virtual curved surface solids are placed by repeating this processing so that virtual curved surface solids are placed in mutually different positions, permitting pixels occupied by different virtual curved surface solids to mutually overlap.

8. The microstructure analysis method according to claim 1, wherein in the step (a), processing to place one of the virtual curved surface solid is performed by placing the parent virtual sphere having the greatest spherical diameter that can be placed so as to fill in the space pixels without overlapping with the matter pixels, and placing one or more of the child virtual spheres such that the center of the child virtual spheres overlaps with the placed parent virtual sphere, and such that pixels occupied by the child virtual spheres do not overlap with the matter pixels and fill in the space pixels, and the multiple virtual curved surface solids are placed by repeating this processing so that pixels occupied by different virtual curved surface solids do not mutually overlap.

9. The microstructure analysis method according to claim 1, wherein in the step (b), based on information relating to the virtual curved surface solids placed in the step (a), the microstructure of the porous body is analyzed by deriving multiple path lengths $L_f$ from one of a predetermined inflow face and a predetermined outflow face of the porous body to the other face following adjacent or overlapping virtual curved surface solids, deriving an average value $L_{fmean}$ of the multiple path lengths $L_{fi}$ and deriving a pressure drop index $P_e$ by $P_e$= (wetted area $A_W$ of space within porous body/pore volume $V_p$ of space within porous body)×(1/porosity $\epsilon$ of porous body)× (average value $L_{fmean}$/distance L between inflow face and outflow face).

10. The microstructure analysis method according to claim 9, wherein in the step (b), the microstructure of the porous body is analyzed by deriving pressure drop $P_S$ per unit thickness of the porous body by $P_S$=constant $\alpha \times P_e^2$+constant $\beta \times P_e$.

11. The microstructure analysis method according to claim 1, wherein in the step (a), processing of placing the multiple virtual curved surface solids, and processing of deriving information relating to flow of a fluid for the each space pixel at the time of the fluid passing through the interior of the porous body by performing fluid analysis based on the porous body data, are performed; and
   in the step (b), the microstructure of the porous body is analyzed based on information relating to the placed virtual curved surface solids and the derived information relating to flow.

12. The microstructure analysis method according to claim 11, wherein in the step (a), by performing fluid analysis regarding a case of inflow of a fluid from a predetermined inflow face of the porous body, and deriving at least flow velocity for the each space pixel as the information relating to flow; and in the step (b), the microstructure of the porous body is analyzed by deriving one or more in-plane uniformity index $\gamma_x$ of flow velocity at a cross-section on the porous body parallel to the inflow face, by the following Expression (1):

[Math. 1]

$$\gamma_x = 1 - \frac{1}{2}\sum_{i=1}^{n} \frac{|u_i - u_{mean}| \cdot A_i}{u_{mean} \cdot A} \qquad \text{Expression (1)}$$

where n: number [count] of virtual curved surface solids within cross-section x: distance [m] between cross-section and inflow face $u_i$: average flow velocity (i=1, 2, ..., n) [m/s] for each of the n virtual curved surface solids at cross-section $u_{mean}$: average value $(=(u_1+u_2+...+u_n)/n)$ [m/s] of average flow velocity $u_i$ at cross-section $A_i$: cross-sectional area (i=1, 2, ..., n) [m²] for each virtual curved surface solid within cross-section A: total cross-sectional area $(=A_1+A_2+...+A_n)$ [m²] of virtual curved surface solids at cross-section.

13. The microstructure analysis method according to claim 12, wherein in the step (b), the microstructure of the porous body is analyzed by deriving the in-plane uniformity index $\gamma_x$ regarding the multiple cross-sections of the porous body, and deriving a spatial uniformity index $\gamma$ of flow velocity at the porous body by the following Expression (2) using the derived in-plane uniformity index $\gamma_x$:

[Math. 2]

$$\gamma = \overline{\gamma_x} \cdot (1 - \delta_\gamma) \qquad \text{Expression (2)}$$

where $\overline{\gamma_x}$: average value of $\gamma_x$ $\delta_\gamma$: standard deviation of $\gamma_x$.

14. The microstructure analysis method according to claim 12, wherein in the step (b), the microstructure of the porous body is analyzed by deriving pressure drop P per unit thickness of the porous body by the following Expression (3) using the derived in-plane uniformity index $\gamma_x$:

[Math. 3]

$$P = \frac{\Delta P_x}{\Delta x} = \left(\frac{200}{3}\frac{1}{D_{hx}^2 \cdot \varepsilon_k}\mu U_x + \frac{7}{6}\frac{1}{D_{hx} \cdot \varepsilon_x^2}\rho U_x^2\right) \cdot \gamma_x^k \qquad \text{Expression (3)}$$

where $\Delta x$: cross-sectional thickness [m] at cross-section at distance x $\Delta P_x$: pressure drop [Pa] at cross-section at distance x $Dh_x$: representative hydraulic diameter [m] of space (pores) at cross-section at distance x $\epsilon_x$: voidage (=number of space pixels/(number of space pixels+number of matter pixels)) at cross-section at distance x $\mu$: viscosity [Pa·s] of fluid $U_x$: flow velocity average value [m/s] at each space pixel at cross-section at distance x $\rho$: density of fluid [kg/m³]

k: constant.

15. The microstructure analysis method according to claim 11, wherein in the step (a), by performing fluid analysis regarding a case of inflow of a fluid from a predetermined inflow face of the porous body, and deriving at least flow velocity for the each space pixel as the information relating to flow; and in the step (b), the microstructure of the porous body is analyzed by deriving through-flow volume Q of the fluid per unit time at the each placed virtual curved surface solid, based on the information relating to the placed virtual curved surface solids and the flow velocity for the each space pixel, and deriving flow-through velocity T of each virtual curved surface solid by T=Q/($\pi$d²/4) based on the derived through-flow volume Q and an equivalent diameter d of the virtual curved surface solid (=6×volume V of virtual curved surface solid/surface area S of virtual curved surface solid).

16. The microstructure analysis method according to claim 15, wherein in the step (b), the microstructure of the porous body is analyzed by classifying the virtual curved surface solids into low-flow-velocity curved surface solids, mid-flow-velocity curved surface solids, and high-flow-velocity curved surface solids, based on the magnitude of the value of the derived flow-through velocity T.

17. The microstructure analysis method according to claim 16, wherein in the step (b), a flow velocity ratio $T_f(=T/T_{in})$ of the derived flow-through velocity T and an average flow velocity $T_{in}$ of the fluid at the inflow face in the fluid analysis is derived, the classification is performed such that, of the placed virtual curved surface solids, virtual curved surface solids where $T_f<2$ are classified as the low-flow-velocity curved surface solids, virtual curved surface solids where $2 \leq T_f \leq 8$ as the mid-flow-velocity curved surface solids, and virtual curved surface solids where $8 \leq T_f$ as the high-flow-velocity curved surface solids.

18. The microstructure analysis method according to claim 1, wherein in the step (b), the microstructure of the porous body is analyzed by an equivalent diameter d of the placed virtual curved surface solids being derived by d=6×(volume V of virtual curved surface solid)/(surface area S of virtual curved surface solid).

19. The microstructure analysis method according to claim 18, wherein in the step (b), the microstructure of the porous body is analyzed by classifying the virtual curved surface solids into small-diameter curved surface solids, mid-diameter curved surface solids, and large-diameter curved surface solids, based on the magnitude of the value of the derived equivalent diameter d.

20. The microstructure analysis method according to claim 19, wherein in the step (b), the classification is performed such that, of the placed virtual curved surface solids, virtual curved surface solids where d<10 μm are classified as the small-diameter curved surface solids, virtual curved surface solids where 10 μm≤d≤25 μm are classified as the mid-diameter curved surface solids, and virtual curved surface solids where 25 μm<d are classified as the large-diameter curved surface solids.

21. A non-transitory computer readable medium for storing a computer program which causes one or multiple computers to realize the steps of the microstructure analysis method according to claim 1.

22. A microstructure analysis device including:

storage unit configured to store porous body data in which is correlated position information representing position of a pixel obtained by a 3 dimensional scan of a porous body, and pixel type information representing whether a space pixel representing that the pixel is space or a matter pixel representing that the pixel is matter;

virtual curved surface solid placing unit configured to take a curved surface solid including a parent virtual sphere and one or more child virtual spheres with which a portion of pixels occupied by the parent virtual sphere overlap as a virtual curved surface solid, and place the multiple virtual curved surface solids so as to fill in the space pixels with curved surface solid pixels which are pixels occupied by the virtual curved surface solid, referencing the porous body data; and microstructure analyzing unit configured to analyze the microstructure of the porous body based on information relating to the placed virtual curved surface solids.

* * * * *